(12) United States Patent
Kore et al.

(10) Patent No.: US 8,304,529 B2
(45) Date of Patent: Nov. 6, 2012

(54) DINUCLEOTIDE MRNA CAP ANALOGS

(75) Inventors: Anilkumar R. Kore, Austin, TX (US); Muthian Shanmugasundaram, Austin, TX (US)

(73) Assignee: Life Technologies Corporation, Carlsbad, CA (US)

( * ) Notice: Subject to any disclaimer, the term of this patent is extended or adjusted under 35 U.S.C. 154(b) by 619 days.

(21) Appl. No.: 12/375,527

(22) PCT Filed: Jul. 10, 2007

(86) PCT No.: PCT/US2007/015896
§ 371 (c)(1),
(2), (4) Date: Nov. 25, 2009

(87) PCT Pub. No.: WO2008/016473
PCT Pub. Date: Feb. 7, 2008

(65) Prior Publication Data
US 2010/0261231 A1    Oct. 14, 2010

Related U.S. Application Data

(60) Provisional application No. 60/820,771, filed on Jul. 28, 2006.

(51) Int. Cl.
*C07H 21/00* (2006.01)
(52) U.S. Cl. .............. 536/25.3; 536/23.1; 536/26.1; 536/26.2; 536/26.21; 536/26.22; 514/43; 514/45; 514/46; 514/47
(58) Field of Classification Search .................. None
See application file for complete search history.

(56) References Cited

U.S. PATENT DOCUMENTS

| 2003/0194759 A1 | 10/2003 | Darzynkiewiz et al. |
| 2005/0287539 A1 | 12/2005 | Labourier et al. |
| 2010/0233757 A1 | 9/2010 | Jemiely et al. |
| 2010/0304389 A1 | 12/2010 | Kore et al. |

FOREIGN PATENT DOCUMENTS

| WO | WO-2008/016473 | 2/2008 |
| WO | WO-2009/058911 | 5/2009 |

OTHER PUBLICATIONS

European Communication in EP Patent Application No. 07810384.3 mailed Nov. 15, 2010.
Office Action in U.S. Appl. No. 12/771,495 mailed on Oct. 15, 2010.
Ex Parte Quayle Action in U.S. Appl. No. 12/771,495 mailed on Apr. 22, 2011.
Office Action in CA Patent Application No. 2,659,301 Mailed Jan. 13, 2011.
Barik, S., "The structure of the 5' terminal cap of the respiratory syncytial virus mRNA", *Journal of General Virology*, vol. 74, No. 3, 1993, 485-490.
Cai, A. et al. "Quantitative assessment of mRNA cap analogues as inhibitors of in vitro translation", *Biochemistry*, vol. 38, No. 26, 1999, 8538-8547.
Jemiality, J. et al., "Novel "anti-reverse" cap analogs with superior translational properties", *RNA*, vol. 9, 2003, 1108-1122.
Kore, A. et al., "Locked Nucleic Acid (LNA)-Modified Dinucleotide mRNA Cap Analogue: Synthesis, Enzymatic Incorporation, and Utilization", *J. Am. Chem. Soc.*, vol. 131, 2009, 6364-6365.
Kore, A.et al., "Synthesis and application of 2'-fluoro-substituted cap analogs", *Bioorganic & Medicinal Chemistry Letters*, vol. 17, 2007, 5295-5299.
International Written Opinion in PCT Patent Application No. PCT/US2007/015896 mailed Dec. 9, 2008.
International Search Report in PCT Patent Application No. PCT/US2007/015896 mailed Feb. 11, 2008 Dec. 9, 2008.
International Preliminary Report on Patentability in PCT Patent Application No. PCT/US2007/015896 mailed Dec. 9, 2008.
International Search Report and Written Opinion in PCT Patent Application No. PCT/US2008/081651 mailed May 8, 2009.
International Preliminary Report on Patentability in PCT Patent Application No. PCT/US2008/081651 mailed May 4, 2010.
Peng, Z. et al. "Synthesis and Application of a Chain-Terminating Dinucleotide mRNA Cap Analog", *Org. Lett.*, vol. 4, No. 2, 2002, 161-164.
Stachelska, A. et al, "Kinetics of the Imidazolium Ring-Opening of mRNA 5'-cap Analogs in Aqueous Alkali", *Collection of Czechoslovak Chemical Communications*, vol. 71, No. 4, 2006, 567-578.
Stepinski, J. et al. "Synthesis and properties of mRNAs containing the novel "anti-reverse" cap analogs 7-methyl(3'-O-methyl)GpppG. and 7-methyl(3'-deoxy)GpppG", *RNA*, vol. 7, No. 10, 2001, 1486-1495.
Stepinski, J. et al. "Synthesis and Properties of P1 ,P2-, P1 ,P3- and P1,P4-Dinucleoside Di-, Tri-and Tetraphosphate MRNA 51-Cap Analogues", *Nucleosides, Nucleotides and Nucelic Acids*, vol. 14, No. 3/5, 1995, 717-721.
Westman, B. "The antiviral drug ribavirin does not mimic the 7methylguanosine moiety of the mRNA cap structure in vitro", *RNA*, vol. 11, No. 10, 2005, 1505-1513.
Worch, R. et al, "Specificity of recognition of mRNA 5' cap by human nuclear cap-binding complex", *RNA*, vol. 11, No. 9, 2005, 1355-1363.

*Primary Examiner* — Patrick Lewis

(57) ABSTRACT

Novel cap analogs which are easily synthesized, resulting in high levels of capping efficiency and transcription and improved translation efficiencies are provided. Such caps are methylated at the N7 position of one or both guanosines of the dinucleotide cap as well as at the 3' position on the ribose ring. Substituent groups on the ribose ring also result in the cap being incorporated in the forward orientation. Also provided are methods useful for preparing capped analogs and using mRNA species containing such analogs are also contemplated herein, as well as kits containing the novel cap analogs.

15 Claims, 11 Drawing Sheets

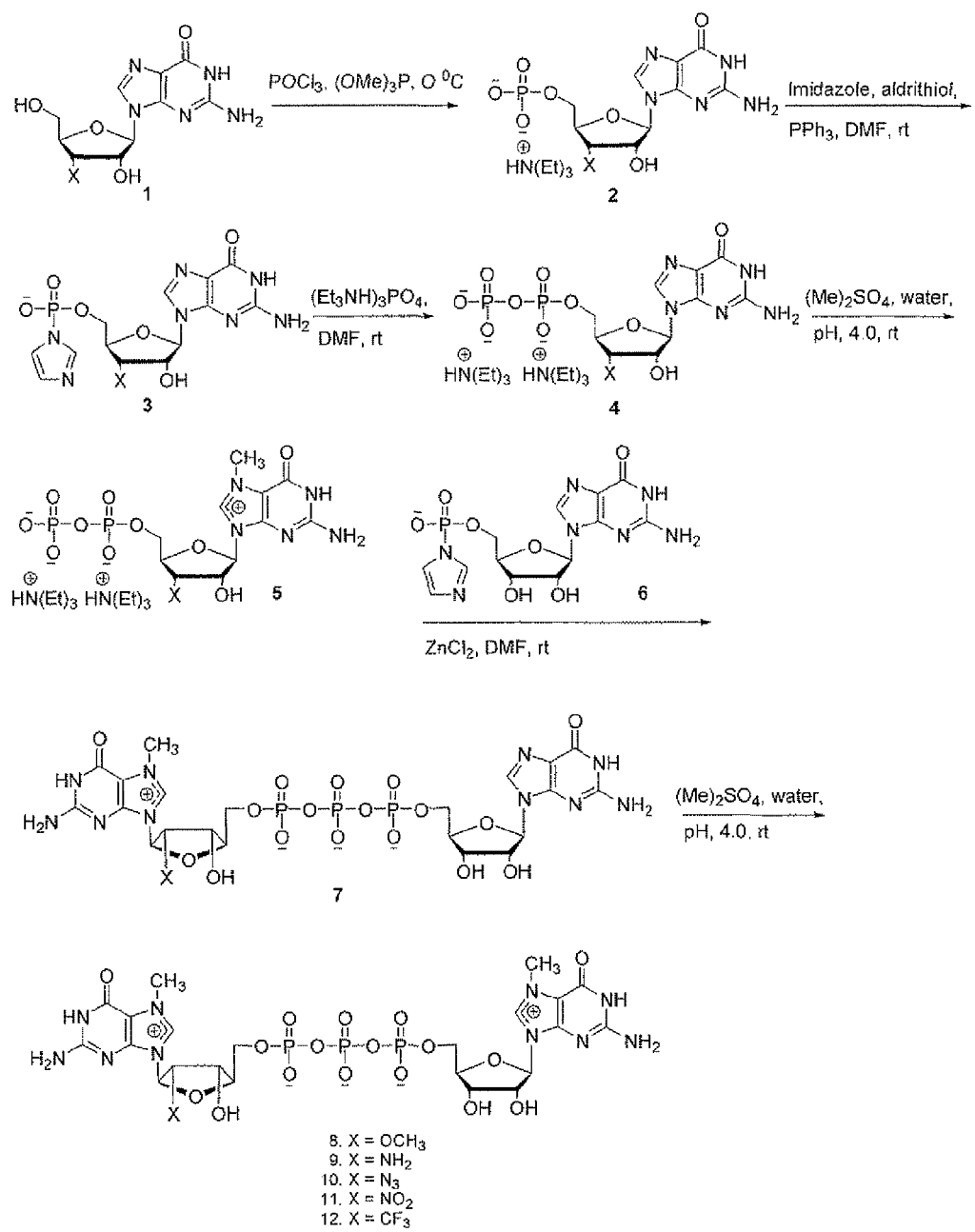
Figure 1: Synthesis of novel double methylated cap analogs (m⁷G[5']ppp[5']m⁷G)

Figure 2: Synthesis of Novel Cap Analog m$^{7,2'F}$G[5]ppp[5']G (2'F-Me-7-G(5')ppp(5')G)
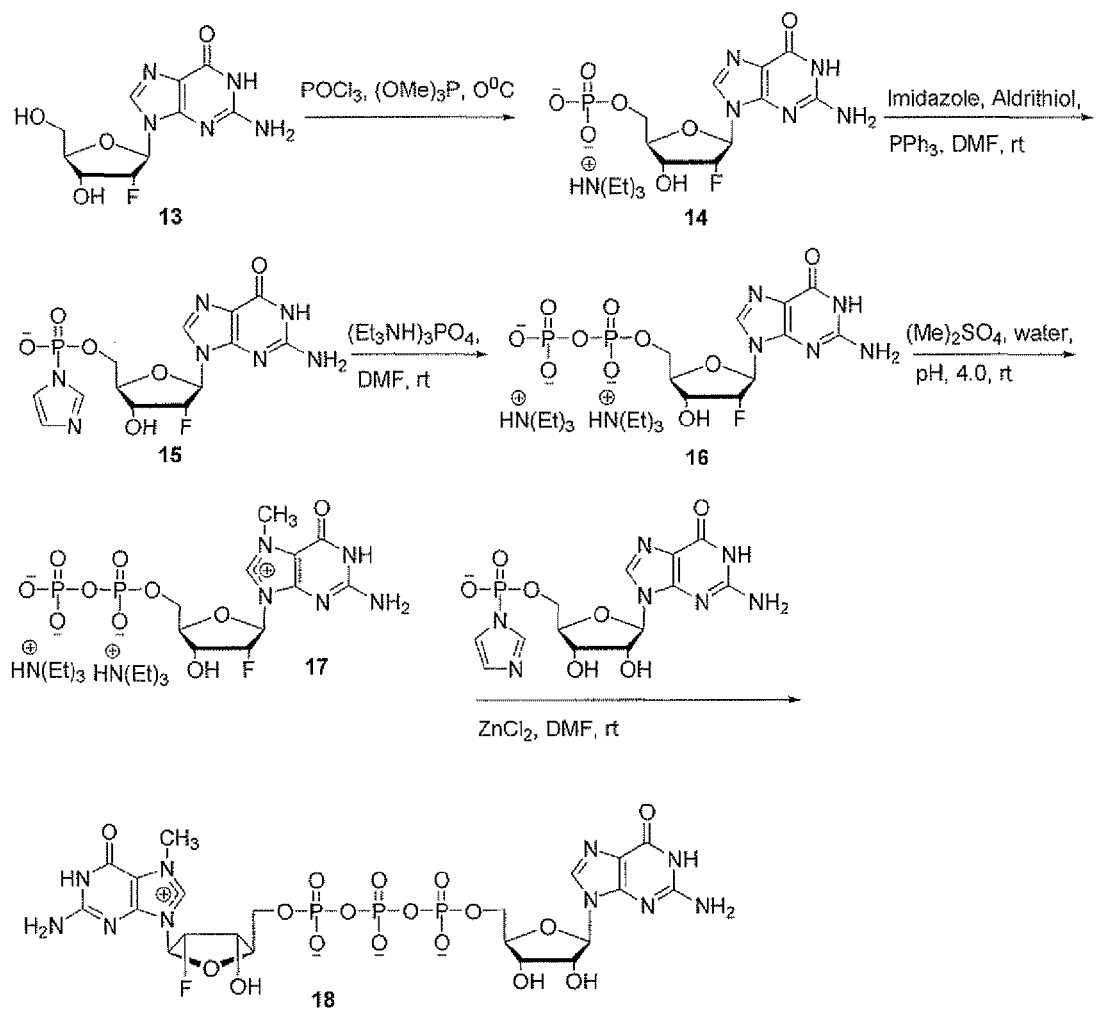

Figure 3. General structure of mCAP
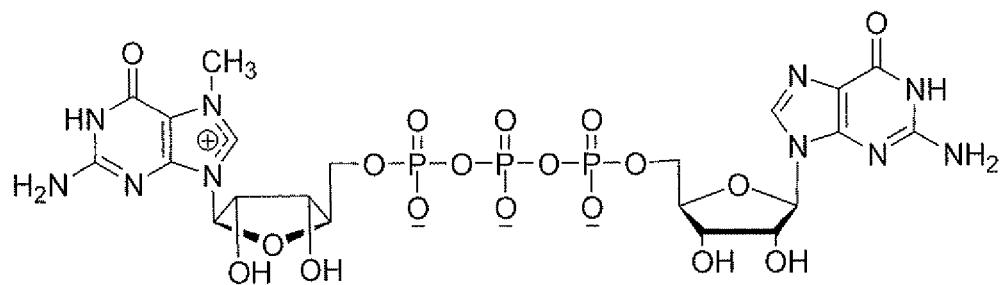
The general cap structure consists of $P$1-guanosine-5'-yl $P$3-7-methylguanosine-5'-yl triphosphate ($m^7$G5'[5']ppp[5']G). The 5'-terminal cap of eukaryotic mRNA, $m^7$G[5']ppp[5']N, (N could be any nucleotide) is necessary for optimal protein translation, pre-mRNA splicing and efficient transport of mRNA from nucleus to the cytoplasm.

Figure 4. Exemplary modified cap analogs

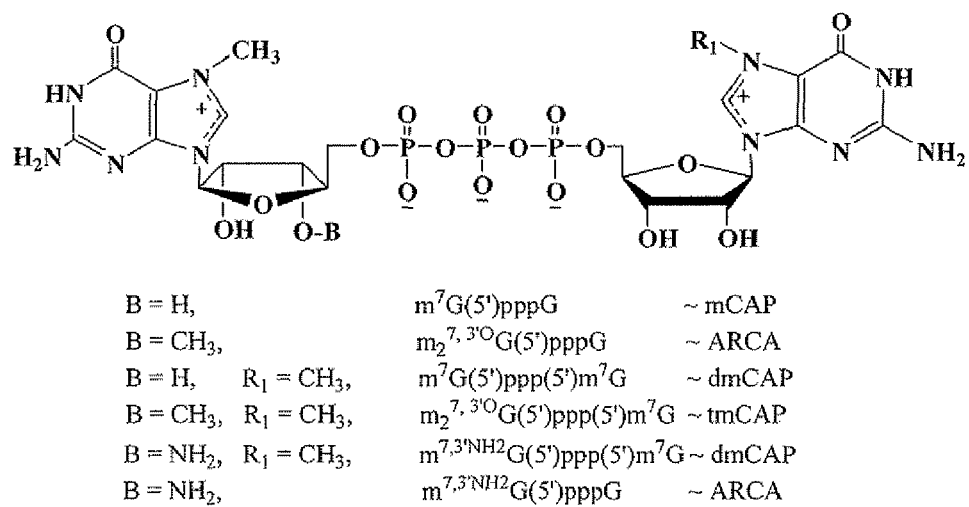

| | | | |
|---|---|---|---|
| B = H, | | m⁷G(5')pppG | ~ mCAP |
| B = CH₃, | | m₂⁷,³'ᴼG(5')pppG | ~ ARCA |
| B = H, | R₁ = CH₃, | m⁷G(5')ppp(5')m⁷G | ~ dmCAP |
| B = CH₃, | R₁ = CH₃, | m₂⁷,³'ᴼG(5')ppp(5')m⁷G | ~ tmCAP |
| B = NH₂, | R₁ = CH₃, | m⁷,³'ᴺᴴ²G(5')ppp(5')m⁷G | ~ dmCAP |
| B = NH₂, | | m⁷,³'ᴺᴴ²G(5')pppG | ~ ARCA |

In addition to the substituents listed above, the 3' hydroxyl group can also be replaced with other electron donating and withdrawing groups.

Figure 5. Digestion of AmbLuc poly A with Blp 1
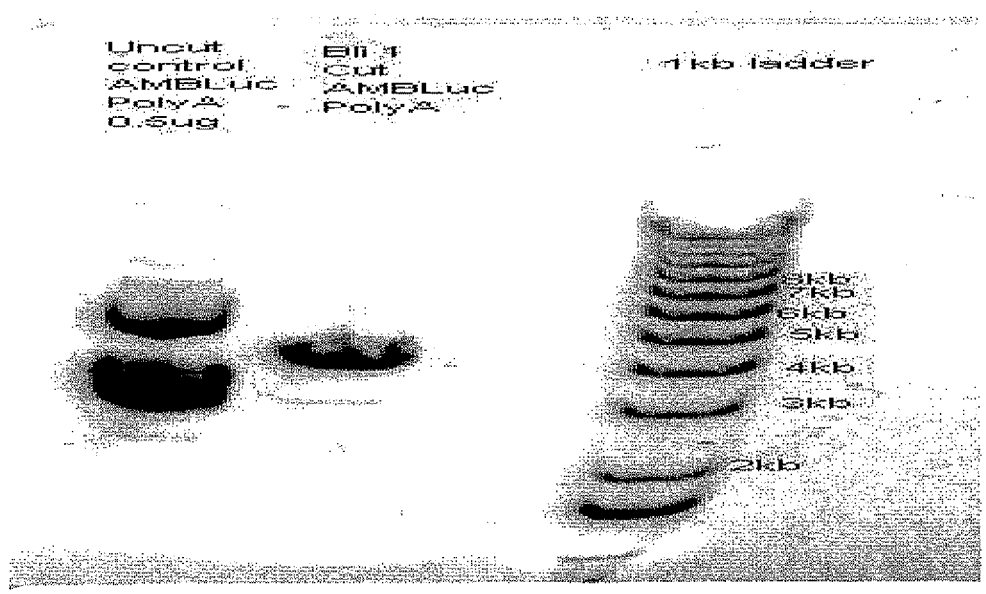
AmbLuc Poly A RNA was subjected to Blp I digestion. In a reaction volume of 100 µl, 50 µg plasmid was digested overnight at 37°C by 80 units Blp I. Analysis of the linearized plasmid was by 0.8% agarose gel.

Figure 6: Yields from transcription reactions with tmCAP & dmCAP analogs by using AmbLuc Poly A RNA vector

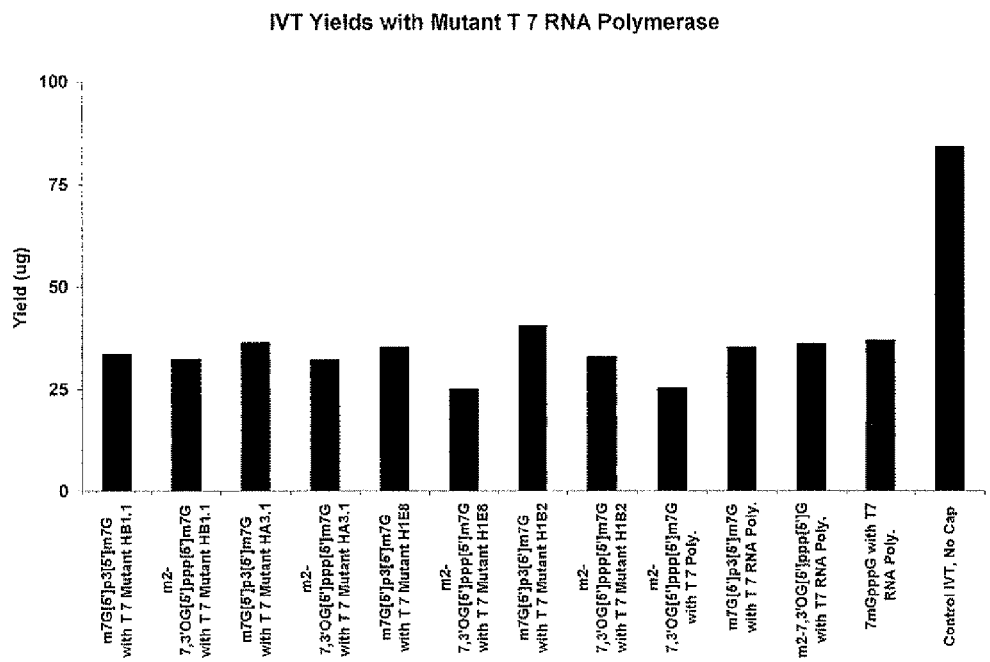

Yields from transcription reactions by using double and triple methylated cap analogs are in agreement with the standard cap mCAP and ARCA. Different T7 mutant enzymes were also used, and yields indicate more transcript than obtained with wild-type enzyme.

Figure 7: Integrity assay of RNAs on an Agilent 2100 Bioanalyzer
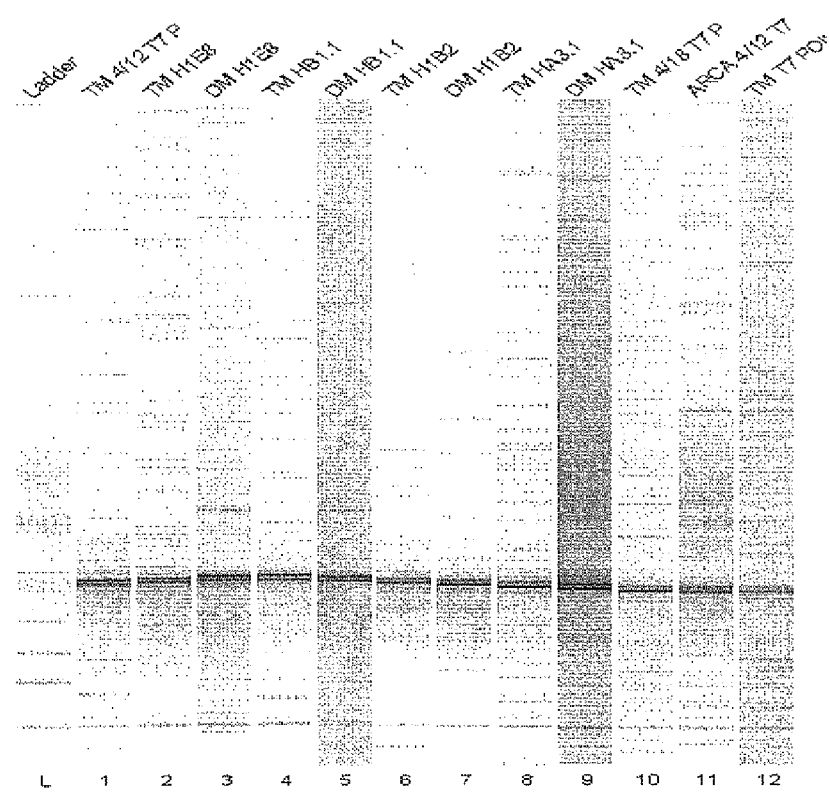
In order to see whether transcribed RNAs from Figure 6 were degraded or deleted, the transcribed mRNAs were analyzed with an Agilent 2100 Bioanalyzer, demonstrating great integrity of capped analogs.

Figure 8: Capping efficiency with modified cap analogs

Gel Shift Assay – In order to determine if the DM & TM cap analog can cap RNA efficiently a transcription reaction followed by a gel shift assay was performed by using a MAXIscript T7 kit. A Gel Shift Assay is an assay to detect specific structure or size changes. When structure change or size change occurs it creates complexes that migrate slower during gel electrophoresis than the original complex. To see this phenomenon the RNA transcripts are run on a 20% denaturing Polyacrylamide/8M Urea gel.

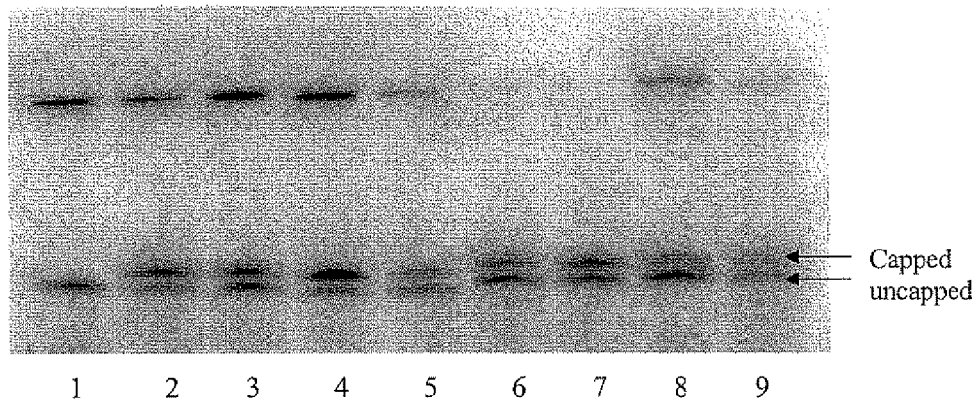

Lanes:

1: Control reaction without Cap; 2: ARCA with T7 Poly (64% capped); 3: DM with T7 Poly (52% capped); 4: mCap with T7 Poly (66% capped); 5: TM Cap with T7 Poly (53% capped); 6: TM Cap with H1B2 mutant (56% capped); 7: DM Cap with H1B2 mutant (55% capped); 8: TM Cap with HA3.1 (46% capped); 9: TM Cap with H1E8 (48% capped)

Figure 9: Luciferase activity with 10 μl lysed Hela cells at different time points after post transfection

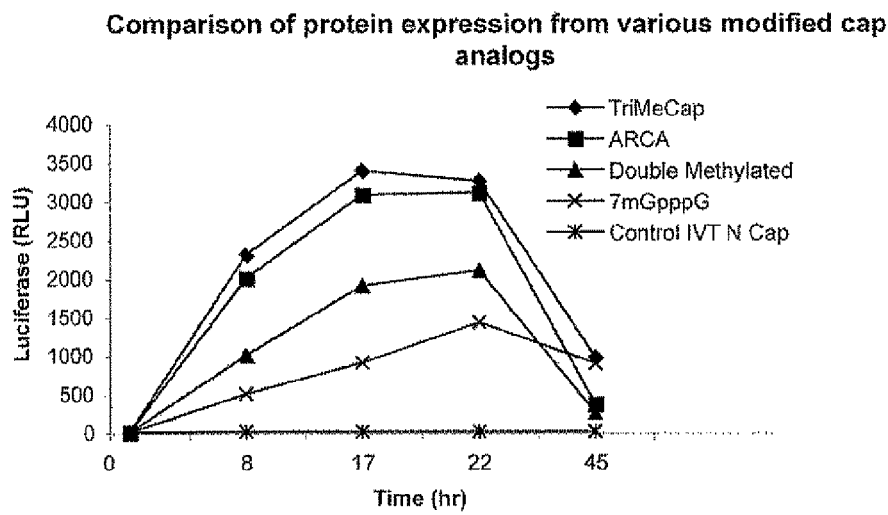

Transcripts containing triple methylated cap analogs are more highly translated in transfected cells. Comparison of protein expression between standard and ARCA, double methylated, and triple methylated capped luciferase RNAs with poly(A) tail at different time points after transfection. mCAP, ARCA, double methylated, and triple methylated capped luciferase *in vitro* transcribed RNA (1μg) was transfected into HeLa cells. Cells were harvested and lysed at 8 hr, 17 hr, 22 hr, and 45 hr post transfection. Luciferase activity was measured and plotted against transfection time. Poly(A) tailed luciferase RNA (1μg) prepared in either a standard mMESSAGE mMACHINE® reaction or mMESSAGE mMACHINE® T7 Ultra reaction was transfected as above. Luciferase activity was measured and plotted against time following transfection.

Figure 10: Yield of transcript by using modified and normal cap analogs.

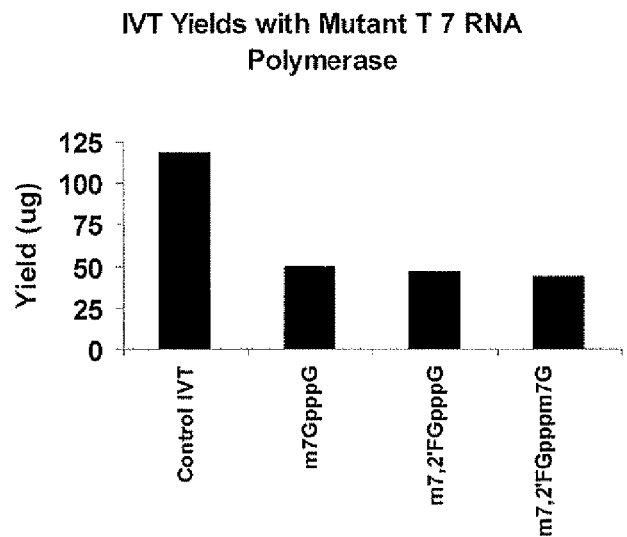

Figure 11: Capping efficiency with Fluorine modified cap analogs

Capping efficiency was determined by using 0.5 mg/mL of pTri β actin vector. Results indicates that normal cap has efficiency i.e., 7mCAP is 60.77% capped, while 2' fluoro ARCA has 70.10% capped, while $N^7$ double methylated version of the fluoro cap has 51.91% of capping efficiency.

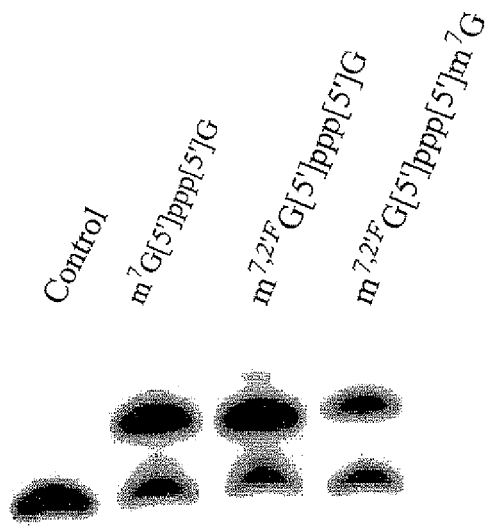

Figure 12: Transfection Assay:

The resulting 5'capped mRNAs were transfected into HeLa cells to determine the functionality and were compared with a known cap analog. 24 h before transfection, 60,000 HeLa cells were plated in 24-well plates. A complex of capped RNA was prepared by mixing 600 ng of RNA, 2.5 µL of TFX-20 ( Promega), and 300 µL of serum-free DMEM in polystyrene tubes and incubated for 15 min at room temperature. After the incubation, media from the pre-plated HeLa cells was removed and 200 µL of the complex was added to each well. The plates were incubated for 1 hour at 37°C, and then 1 mL of pre-warmed media with serum was added. The transfected plates were incubate at 37°C for different time points. Cells were harvested and lysed at 5, 10, 15, 20, 25, 35, and 40 hours. The cells are harvested by removing the media and adding 100 µL of 1X passive lysis buffer (Promega). The plate was mixed carefully to disrupt the cells and samples were read on POLARstar OPTIMA Luminometer (BMG Labtech) after adding the Luciferase Assay reagent (Promega).

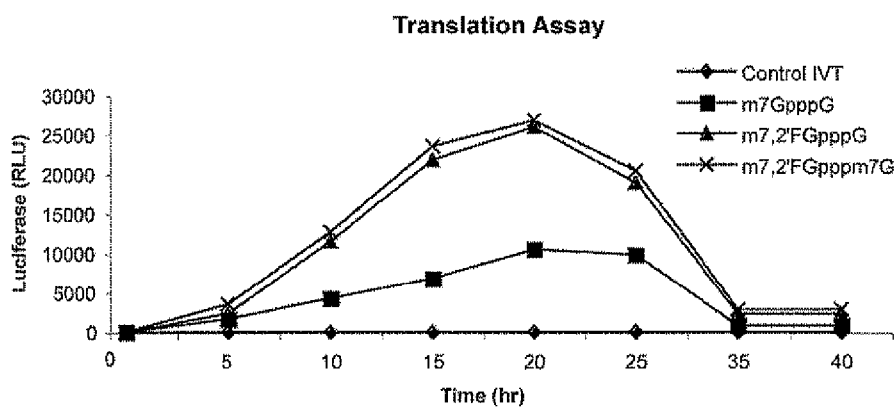

DINUCLEOTIDE MRNA CAP ANALOGS

CROSS-REFERENCE TO RELATED APPLICATIONS

The present application is a National Stage of PCT/US2007/015896, filed Jul. 10, 2007, which claims priority benefit from earlier filed U.S. Provisional Application No. 60/820,771, filed Jul. 28, 2006, both of which are herein incorporated by reference in their entities.

STATEMENT REGARDING FEDERALLY FUNDED SPONSORED RESEARCH OR DEVELOPMENT

Work described herein was funded at least in part by an SBIR grant (SBIR Phase II, No. R44GM070156-02) awarded by National Institutes of Health. The U.S. Government may therefore have certain rights therein.

INTRODUCTION

Eukaryotic mRNAs bear a "cap" structure at their 5'-termini that is well known to play an important role in translation. Naturally occurring cap structures consist of a 7-methyl guanosine that is linked via a triphosphate bridge to the 5'-end of the first transcribed nucleotide, resulting in $m^7G(5')ppp(5')$ N, where N is any nucleotide. The mRNA cap plays an important role in gene expression. It protects the mRNAs from degradation by exonucleases, enables transport of RNAs from the nucleus to the cytoplasm, and participates in assembly of the translation initiation complex. $m^7G(5')ppp(5')G$ (mCAP) has been used as the primer in transcription with T7 or SP6 RNA polymerase in vitro to obtain RNAs having a cap structure in their 5'-termini. In vivo, the cap is added enzymatically. However, over the past 20 years or so, numerous studies have required the synthesis of proteins in an in vitro translation extract supplemented with in vitro synthesized mRNA. The prevailing method for the in vitro synthesis of capped mRNA employs a pre-formed dinucleotide of the form $m^7G(5')ppp(5')G$ as an initiator of transcription. A disadvantage of using mCAP, a pseudosymmetrical dinucleotide, has always been the propensity of the 3'-OH of either the G or $m^7G$ ($m^7Guo$) moiety to serve as the initiating nucleophile for transcriptional elongation. This leads to the synthesis of two isomeric RNAs of the form $m7G(5')pppG(pN)_n$ and $G(5')ppp7G(pN)_n$, in approximately equal proportions, depending upon the ionic conditions of the transcription reaction. This may be problematic for various downstream processes, such as in vitro translation or crystallization studies.

Unmethylated cap analog is a modified cap analog in which the methyl group on the guanosine is removed. The selective procedure for methylation of guanosine at N7 and 3'O-methylation and 5' diphosphate synthesis was established (Kore, A. and Parmar, G. *Nucleosides, Nucleotides, and Nucleic Acids,* 25:337-340, 2006 and Kore A. R., et al. *Nucleosides Nucleotides Nucleic Acids* 2006 25(3): 307-14. The Anti-Reverse Cap Analog (ARCA) is a modified cap analog in which the 3' OH group is replaced with OCH3. ARCA and triple-methylated cap analogs are incorporated in the forward orientation.

In the cell, the cap is added in the nucleus and is catalyzed by the enzyme guanylyl transferase. The addition of the cap to the 5' terminal end of RNA occurs after transcription but immediately after transcription initiation so that it is almost impossible to detect. The terminal nucleoside is always a guanine, and is in the reverse orientation to all the other nucleotides, i.e., 5'Gppp5'GpNpNp . . . and the cap contains two nucleotides, connected by a 5'-5' triphosphate linkage.

Transcription of RNA usually starts with a nucleoside triphosphate (usually a purine, A or G). When transcription occurs in vitro, it typically includes a phage RNA polymerase such as T7, T3 or SP6, a DNA template containing a phage polymerase promoter, nucleotides (ATP, GTP, CTP and UTP) and a buffer containing magnesium salt. The synthesis of capped RNA includes the incorporation of a cap analog (e.g., N7 methyl GpppG or m7GpppG) in the transcription reaction. Excess m7GpppG to GTP (4:1) favors to increase the opportunity that each transcript will have a 5' cap. The mMESSAGE mMACHINE© kit from Ambion (Ambion, Inc., Austin, Tex., a business of Applied Biosystems) recommends this ratio and will typically yield 80% capped RNA to 20% uncapped RNA, although total yields of total RNA are lower as GTP concentration becomes rate limiting as GTP is necessary for the elongation of the transcript.

The 5' cap structure enhances the translation of mRNA by helping to bind the eukaryotic ribosome and assuring recognition of the proper AUG initiator codon. This function may vary with the translation system and with the specific mRNA being synthesized. The consensus sequence 5'-GCCAC-CAUGG-3' SEQ ID NO: 1, also known as the "Kozak" sequence, is considered to be the strongest ribosomal binding signal in eukaryotic mRNA. For efficient translation initiation, the key elements are the G residue at the +1 position and the A residue at the −3 position.

During translation the cap is bound by translation initiation factor eIF-4E and the CBC recruits additional initiation factors. Decapping is catalyzed by proteins dcp1 and dcp2 which compete with eIF-4E to bind to the cap. Translation results in amino acids as encoded by the mRNA to join together to form a peptide and occurs as three processes, initiation, elongation and termination. Initiation in eukaryotes involves attachment of a ribosome which scans the mRNA for the first methionine codon. Elongation proceeds with the successive addition of amino acids until a stop codon is reached, terminating translation.

Capped RNA encoding specific genes can be transfected into eukaryotic cells or microinjected into cells or embryos to study the effect of translated product in the cell or embryo. If uncapped RNA is used, the RNA in these experiments is rapidly degraded and the yield of translated protein is much reduced.

Isolated dendritic cells from a patient can be transfected with capped RNA encoding immunogen. The dendritic cells translate the capped RNA into a protein that induces an immune response against this protein. In a small human study, immunotherapy with dendritic cells loaded with CEA capped RNA was shown to be safe and feasible for pancreatic patients (Morse et al. *Int. J. Gastroinstest. Cancer,* 32:1-6, 2002). It was also noted that introducing a single capped RNA species into immature dendritic cells induced a specific T-cell response (Heiser et al. *J. Clin. Invest.,* 109:409-417, 2002.

The recent literature reveals that chemical modification of m7Guo at either the 2' or 3' OH group results in the cap being incorporated solely in the forward orientation, even though the 2' OH group does not participate in the phosphodiester bond. This observation has prompted investigation of 2' and 3' OH modifications of m7Guo as well as modifications of m7Guo to create double- and triple-methylated cap analogs.

SUMMARY

A composition is provided comprising:

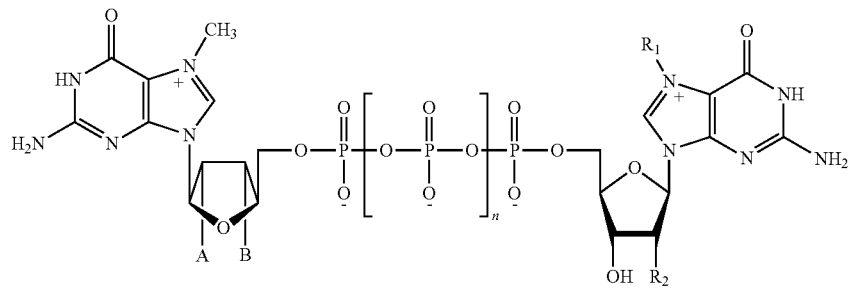

wherein A is selected from a halogen, OH, $OCH_3$, H, tert-butyldimethylsilyl and 2',3'-O-isopropylidene, B is selected from a halogen, OH, $OCH_3$, $NH_2$, $N_3$, $NO_2$, $CF_3$, CHO, S, tert-butyldimethylsilyl, LNA, and 2',3'-O-isopropylidene; $R_1$ is $CH_3$ or void, $R_2$ is selected from OH, $OCH_3$ and a halogen, n is 1, 2 or 3, and when B is OH or $OCH_3$, $R_1$ is void, and $R_2$ is OH, then A is neither OH nor $OCH_3$, and when A, B and $R_2$ are OH, $R_1$ is not $CH_3$.

An anti-reverse cap analog composition is also provided which is represented by the formula:

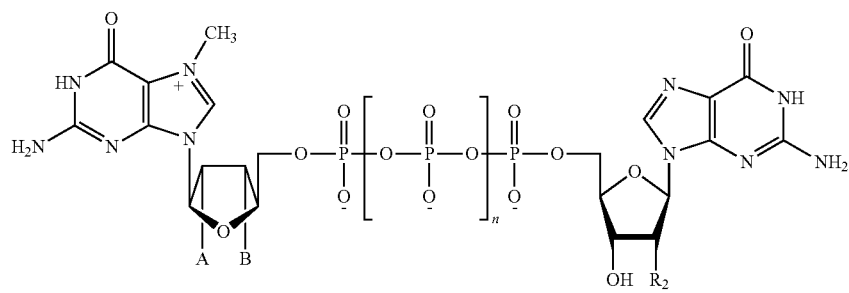

wherein A is selected from a halogen, OH, $OCH_3$, H, tert-butylditnethylsilyl and 2',3'-O-isopropylidene, B is selected from a halogen, OH, $OCH_3$, $NH_2$, $N_3$, $NO_2$, CHO, S, tert-butyldimethylsilyl, LNA, and 2',3'-O-isopropylidene, $R_1$ is void, $R_2$ is selected from OH, $OCH_3$ and a halogen, n is 1, 2 or 3; and when A is either OH or $OCH_3$, then $R_2$ is not OH.

A double-methylated cap analog composition is also provided as represented by the formula:

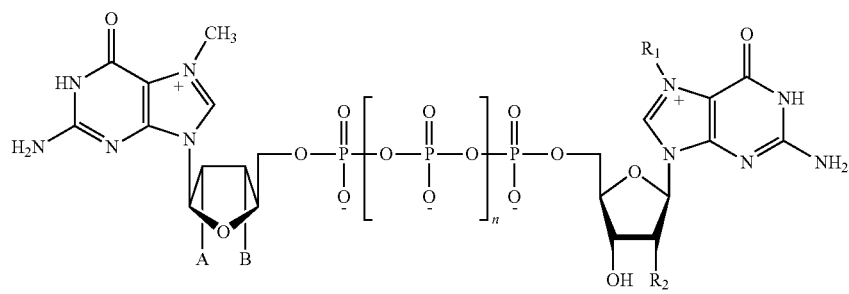

wherein A is selected from a halogen, OH, OCH₃, H, -and 2',3'-O-isopropylidene, B is selected from CF₃, OH, OCH₃, NH₂, N₃, NO₂, CHO, LNA, and 2',3'-O-isopropylidene, R₁ is CH₃, R₂ is selected from OH, OCH₃ and a halogen, n is 1, 2 or 3, and when A is OH, R₂ is not OH.

A triple-methylated cap analog is provided as represented by the formula:

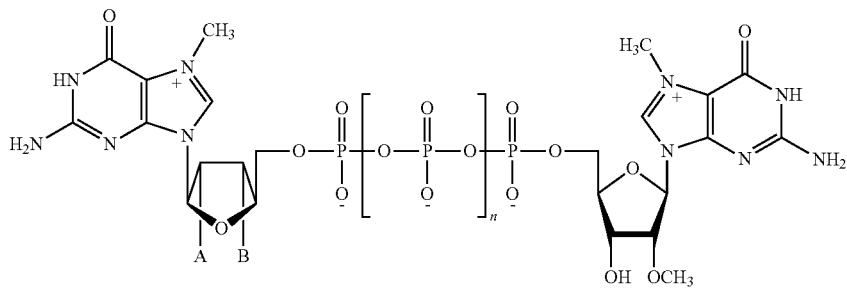

wherein A is selected from OH and OCH₃, B is selected from OH and OCH₃, and n is, 1, 2 or 3.

When A or B are a halogen, the halogen can be fluorine, chlorine, bromine or iodine. The phophodiester linkage between the guanosine molecules can be a triphosphate linkage, a tetraphosphate linkage or a pentaphosphate linkage.

An RNA molecule is also provided which has incorporated at its 5' end one of the structures as described above.

Also provided is a kit for capping an RNA transcript comprising the formula:
a) a cap analog have the structure as recited in claim 1:

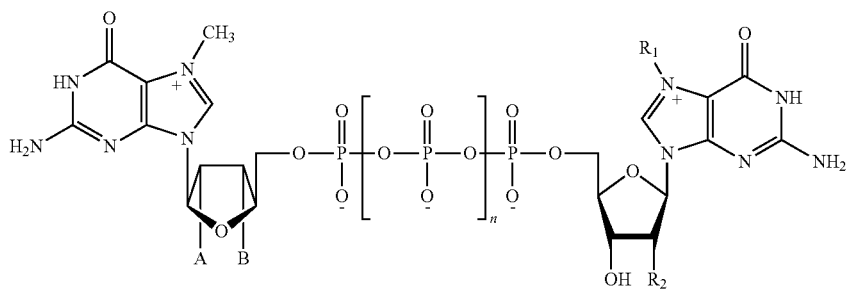

wherein a is selected from a halogen, OH, OCH₃, H, TBDMS and 2',3'-O-isopropylidene; B is selected from OH, OCH₃, NH₂, N₃, NO₂, CF₃, CHO, halogen, S, TBDMS, LNA, and 2',3'-O-isopropylidene; R₁ is CH₃ or void; R₂ is selected from OH, OCH₃ and a halogen; and n is, 1, 2 or 3; wherein when B is OH or OCH₃, and R₁ is void, A is neither OH nor OCH₃ if R₂ is OH and b). RNA polymerase. The kit may also comprise nucleotides, ribonuclease inhibitor, enzyme buffer, and nucleotide buffer.

Also provided is a method of synthesizing a dinucleotide cap analog comprising: a) providing a first nucleoside comprising at least one of a 2' substituent and a 3' substituent on the ribose ring, b) phosphorylating the first nucleoside, forming a first nucleotide, c) methylating the first nucleotide, d) adding a phosphorylated second nucleotide optionally comprising a 2' ribose ring substituent, and e) linking said first nucleotide with said second nucleotide, forming a dinucleotide cap analog.

These and other features of the present teachings are set forth herein.

BRIEF DESCRIPTION OF THE FIGURES

The skilled artisan will understand that the drawings, described below, are for illustration purposes only. The drawings are not intended to limit the scope of the present teachings in any way.

FIG. 1 illustrates the synthesis scheme for novel double-methylated cap analogs.

FIG. 2 illustrates the synthesis of a novel ARCA.

FIG. 3 illustrates the basic RNA cap structure (mCAP) consisting of P1-guanosine-5'-yl P3-7-methylguanosine-5'-yl triphosphate (m⁷G5'ppp5'G).

FIG. 4 illustrates exemplary modified cap analogs. Modifications are at either or both G7 positions and/or the 3' ribose position of the m⁷ Guo.

FIG. 5 shows the results of digestion of AmbLuc poly A RNA with Blp 1

FIG. 6 graphically depicts yields from transcription reactions by using double- and triple-methylated cap analogs in an AmbLuc poly A vector.

FIG. 7 shows the high level of RNA integrity when capped as analyzed with an Agilent 2100 Bioanalyzer.

FIG. 8 show the capping efficiency of RNA in a transcription reaction by a gel shift assay.

FIG. 9 illustrates the comparison of protein expression between standard and ARCA, double-methylated, and triple-methylated capped luciferase RNAs with poly(A) tail at different time points after transfection.

FIG. 10 illustrates transcript yield by using modified and normal cap analogs.

FIG. 11 illustrates capping efficiency with fluorine-modified cap analogs

FIG. 12 illustrates transfection efficiency of fluorine-modified cap analogs in a luciferase assay

DESCRIPTION OF VARIOUS EMBODIMENTS

For the purposes of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in interpreting the document where the term is originally used). The use of "or" herein means "and/or" unless stated otherwise or where the use of "and/or" is clearly inappropriate. The use of "a" herein means "one or more" unless stated otherwise or where the use of "one or more" is clearly inappropriate. The use of "comprise," "comprises," "comprising," "include," "includes," and "including" are interchangeable and not intended to be limiting.

As used throughout, "Me" is equivalent to "$CH_3$", "$OCH_3$" or "OMe" denotes an oxygen atom bound to a methyl group, "CHO" denotes a carbon atom, C, bonded to a hydrogen atom, H, and double-bonded to an oxygen atom, O, (O=CH—) and "Et" denotes "$C_2H_5$".

As used herein, the term "ARCA" or anti-reverse cap analog refers to a modified cap analog in which the 3' OH group is replaced with OCH3. The structure is represented as $m_2^{7,3'}$(5')Gppp(5')G.

As used herein, the term "cap" refers to a non-extendible di-nucleotide that facilitates translation or localization, and/or prevents degradation of an RNA transcript when incorporated at the 5' end of an RNA transcript, typically having an m7GpppG or m7GpppA structure. It consists in nature of the modified base 7-methylguanosine joined in the opposite orientation, 5' to 5' rather than 5' to 3', to the rest of the molecule via three phosphate groups i.e., PI-guanosine-5'-yl P3-7-methylguanosine-5'-yl triphosphate ($m^7$G5'ppp5'G).

As used herein, the term "cap analog" refers to a structural derivative of an RNA cap that may differ by as little as a single element.

As used herein, the term "double-methylated" cap (dm-CAP) refers to each guanosine molecule of a dinucleotide cap in which each N7 position contains a —$CH_3$ group. It is illustrated as $m^7$ (5')Gppp(5')$m^7$G.

As used herein, the term "triple-methylated" cap (tm-CAP) refers to the presence of a —$CH_3$ group on each N7 position of the guanosine molecules of a dinucleotide cap and an additional $OCH_3$ group in the 2' or 3' position of the ribose ring of one of the guanosine molecules. tmCAPs are illustrated as $n_2^{7,2'O}$ (5')Gppp(5')$m^7$G, $m_2^{7,3'O}$ (5')Gppp(5')$m^7$G, $m^7$(5')Gppp(5') $m_2^{7,2'O}$ G, or $m^7$(5')Gppp(5') $m_2^{7,3'O}$G.

As used herein, the term "enzymatically incorporatable" means that a nucleotide is capable of being enzymatically incorporated onto the terminus, e.g. 3' terminus, of a polynucleotide chain, or internally through nick-translation of a polynucleotide chain, through action of a template-dependent or template-independent polymerase enzyme. A nucleotide-5'-triphosphate is an example of an enzymatically incorporatable nucleotide.

As used herein, the term "enzymatically extendable" or "3' extendable" means a nucleotide or polynucleotide that is capable of being appended to a nucleotide or polynucleotide by enzyme action. A polynucleotide containing a 3' hydroxyl group is an example of an enzymatically extendable polynucleotide.

As used herein, the term "halogen" refers to nonmetal elements of Group 7A of the Periodic Table of the Elements comprising fluorine, F, chlorine, Cl, bromine, Br, iodine, I, and astatine, At. Halogens are monovalent, readily form negative ions and occur as compounds or ions.

As used herein, the term "locked nucleic acid" (LNA) refers to a bridge between the 2'O and 4'C methylene bicyclonucleotide monomers.

As used herein, the term "nucleobase" refers to a nitrogen containing heterocyclic moiety nucleobase. Non-limiting examples of suitable nucleobases include: adenine, cytosine, guanine, thymine, uracil, 5-propynyl-uracil, 2-thio-5-propynyl-uracil, 5-methylcytosine, pseudoisocytosine, 2-thiouracil, 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(8-aza-7-deazaadenine).

As used herein, the term "nucleoside" refers to a compound consisting of a nucleobase linked to the C-1' carbon of a ribose sugar or analog thereof. The ribose or analog may be substituted or unsubstituted. Substituted ribose sugars include, but are not limited to, those riboses in which one or more of the carbon atoms, preferably the 3'-carbon atom, is substituted with one or more of the same or different substituents such as —R, —OR, —NRR or halogen (e.g., fluoro, chloro, bromo, or iodo), where each R group is independently —H, $C_1$-$C_6$ alkyl or $C_3$-$C_{14}$ aryl. Particularly, riboses are ribose, 2'-deoxyribose, 2',3'-dideoxyribose, 3'-haloribose (such as 3'-fluororibose or 3'-chlororibose) and 3'-alkylribose. Typically, when the nucleobase is A or G, the ribose sugar is attached to the $N^9$-position of the nucleobase. When the nucleobase is C, T or U, the pentose sugar is attached to the $N^1$-position of the nucleobase (Kornberg and Baker, *DNA Replication*, $2^{nd}$ Ed., Freeman, San Francisco, Calif., (1992)). Examples of ribose analogs include arabinose, 2'-O-methyl ribose, and locked nucleoside analogs (e.g., WO 99/14226), for example, although many other analogs are also known in the art.

As used herein, the term "nucleotide" refers to a phosphate ester of a nucleoside as a monomer unit or within a polynucleotide.

As used herein, the term "nucleotide triphosphate" refers to a nucleotide with a triphosphate ester group at the 5' position.

As used herein, nucleosides and/or nucleotides of the present teachings can comprise "natural sugars" (i.e., -ribose, 2'-deoxyribose, and the like) or sugar analogues.

As used herein, the term "sugar analog" refers to analogs of the sugar ribose. Exemplary ribose sugar analogs include, but are not limited to, substituted or unsubstituted furanoses having more or fewer than 5 ring atoms, e.g., erythroses and hexoses and substituted or unsubstituted 3-6 carbon acyclic sugars. Typical substituted furanoses and acyclic sugars are those in which one or more of the carbon atoms are substituted with one or more of the same or different —R, —OR, —NRR or halogen groups, where each R is independently —H, ($C_1$-$C_6$) alkyl or ($C_1$-$C_{14}$) aryl. Examples of substituted furanoses having 5 ring atoms include but are not limited to 2'-deoxyribose, 2'-($C_1$-$C_6$)alkylribose, 2'-($C_1$-$C_6$)alkoxyribose, 2'-(C$_5$-C$_{14}$)aryloxyribose, 2',3'-dideoxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C$_1$-C$_6$)alkylribose, 2'-deoxy-3'-(C$_1$-C$_6$)alkoxyribose, 2'-deoxy-3'-(C$_5$-C$_{14}$)aryloxyribose, 3'-(C$_1$-C$_6$)alkylribose-5'-triphosphate, 2'-deoxy-3'-(C$_1$-C$_6$)alkylribose-5'-triphosphate, 2'-deoxy-3'-(C$_1$-C$_6$)alkoxyribose-5'-triphosphate, 2'-deoxy-3'-(C$_5$-C$_{14}$)atyloxyribose-5'-triphosphate, 2'-deoxy-3'-haloribose-5'-triphosphate, 2'-deoxy-3'-aminoribose-5'-triphosphate, 2',3'-dideoxyribose-5'-triphosphate or 2',3'-didehydroribose-5'-triphosphate. Further sugar analogs also include so called locked nucleic acids (LNAs) having the structure

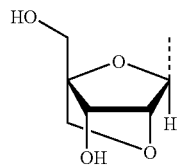

and those described in Wengel, et al. WO 99/14226, incorporated herein by reference.

As used herein, the terms "polynucleotide", "oligonucleotide" and "nucleic acid" are used interchangeably and refer to single stranded and double stranded polymers of nucleotide monomers, including ribonucleotides (RNA) and 2'-deoxyribonucleotides (DNA) linked by internucleotide phosphodiester bond linkages. A polynucleotide may be composed entirely of deoxyribonucleotides, entirely of ribonucleotides or chimeric mixtures thereof.

As used herein, the term "terminator" means an enzymatically ineorporatable nucleotide which prevents subsequent incorporation of nucleotides to the resulting polynucleotide chain and thereby halts polymerase-mediated extension. Typical terminators lack a 3'-hydroxyl substituent and include 2',3'-dideoxyribose, 2',3'-didehydroribose, and 2',3'-dideoxy-3'-haloribose, e.g. 3'-deoxy-3'-fluoro-ribose or 2',3'-dideoxy-3'-fluororibose, for example. Alternatively, a ribofuranose analog can be used, such as 2',3'-dideoxy-β-D-ribofuranosyl, β-D-arabinofuranosyl, 3'-deoxy-β-D-arabinofuranosyl, 3'-amino-2',3'-dideoxy-β-D-ribofuranosyl, and 2',3'-dideoxy-3'-fluoro-β-D-ribofuranosyl (see, for example, Chidgeavadze et al., Nucleic Acids Res., 12: 1671-1686 (1984), and Chidgeavadze et al. FEB. Lett., 183: 275-278 (1985)). Nucleotide terminators also include reversible nucleotide terminators (Metzker et al. Nucleic Acids Res., 22(20):4259 (1994)).

As used herein, the term "nonextendable" or "3' nonextendable" refers to the fact that a terminator is incapable, or substantially incapable, of being extended in the 3' direction by a template-dependent DNA or RNA polymerase.

As used herein, the term "TBDMS refers to tert-butyldimethylsilyl.

As used herein, the term "void" refers to the absence of a substituent group at the R$_1$ position of the cap analog. The lack of a substituent group results in no positive chare o the imidazole ring. In one embodiment the substituent group may be a CH$_3$ group. When the CH$_3$ group is present, there is a positive charge on the imidazole ring.

Cap analog is used for the synthesis of 5' capped RNA molecules in in vitro transcription reactions. Substitution of cap analog for a portion of the GTP in a transcription reaction results in the incorporation of the cap structure into a corresponding fraction of the transcripts. Capped mRNAs are generally translated more efficiently in reticulocyte lysate and wheat germ in vitro translation systems. It is important that in vitro transcripts be capped for microinjection experiments because uncapped mRNAs are rapidly degraded. Cap analogs are also used as a highly specific inhibitor of the initiation step of protein synthesis.

In one embodiment novel ARCA, double- and triple-methylated cap analogs are disclosed. The cap structures have been synthesized and designed to attach in the forward orientation, i.e., 5'Gppp5'GpNpNp . . . . The resulting novel cap analogs have been demonstrated to improve the yield and efficiency of transcription compared to the standard cap analog as shown in FIGS. 6, 8, and 10.

These analogs also have novel substituent groups at the 2' and/or 3' positions of the ribose ring which also resulting in attaching of the cap in the forward orientation. In one embodiment, fluorine attached at the 2' or 3' position of the ribose ring has been shown to improve both capping efficiency and translation efficiency as shown in FIGS. 11 and 12.

The synthesis of capped RNA which is not only efficiently capped and yields high levels of transcribed RNA is an area of unmet need. One approach which is being used by Ambion is disclosed in US patent application 2005/0287539, incorporated herein by reference. The synthesis of cap analogs which incorporate in only the forward orientation will improve transcription and translation efficiency.

The teachings of Darynkiewicz et al. in U.S. Pat. No. 7,074,596 have attempted to present synthesis methods and methylation methods for anti-reverse cap analogs. The method of methylation as taught was not reproducible in our hands, neither was the synthesis of a linker and methods for linking the nucleotides.

Thus, there exists in the art an unmet need for high yield transcription reactions that efficiently synthesize RNA. The resulting RNA finds use in a variety of applications, including ribozyme, antisense and biophysical studies, and gene array analysis. Additionally, capped RNA transcripts are used for applications requiring protein synthesis such as in vivo expression (e.g., microinjection, transfection and infection experiments) and in vitro translation.

In order to overcome the problem of synthetic mCAP attaching to RNA in the reverse orientation around 50% of the time, when NTPs and cap RNA are present in comparable concentrations, the present application teaches chemically convenient and reproducible methods for the synthesis of modified cap analog, anti-reverse cap analog (ARCA), and double- and triple-methylated cap analogues (FIGS. 1 and 2).

The design and synthesis of novel cap analogs such as m7,2'FG[5']ppp[5']G and m7,2'FG[5']ppp[5']m7G, a double-methylated cap, in which various moieties at the 2' and 3' positions on the ribose ring have been substituted are presented (FIG. 2).

Also discovered and synthesized are triple-methylated caps. Such caps include m27,2'OG[5']ppp[5']m7G, m27, 2'OG[5']ppp[5'] m2' OG, m27,3'OG[5']ppp[5']m7G, and m27,2'OG[5']ppp[5'] m27,2'OG. Additionally, details of the compatibility of new, modified cap analogs with respect to transcription, capping and translation efficiency by using HeLa cells in comparison with the standard and conventional ARCA cap analog is presented.

Structures were confirmed by $^1$H NMR and $^{31}$P NMR. Transcripts produced with T7 RNA polymerases using "anti-reverse" cap analogs (ARCAs) were of the predicted length and indistinguishable in size and homogeneity from those produced with m$^7$GpppG. Transfection assays were performed by using standard cap analog-capped and ARCA-capped luciferase in in vitro transcribed RNA with HeLa cells. Finally, luciferase activity was measured and revealed that ARCA-capped transcripts were 2.2 to 2.5 fold higher than that of m$^7$GpppG-capped transcripts. This finding also suggest that the presence of reverse caps in conventional in vitro-synthesized mRNA reduces their translation efficiency.

Those having ordinary skill in the art will understand that many modifications, alternatives, and equivalents are possible.

All such modifications, alternatives, and equivalents are intended to be encompassed herein.

Materials and Methods

Reagents

All of the reagents and solvents are used as such without further purification, unless otherwise stated. Guanosine 5'-diphosphate, Dimethyl sulfate, anhydrous dimethylformamide, 2,2'-dithiodipyridine (Aldrithiol), Triphenylphosphine, trimethylphosphate (($OMe)_3P$), phosphorous oxychloride, phosphorous pentoxide, orthophosphoric acid, anhydrous methylene chloride, dichloromethane, Tributylamine, anhydrous pyridine were purchased from Sigma-Aldrich Co. 3'-O-Me-Guanosine is available from Chemgene, Boston, Mass. Imidazolide GMP, Imidazolide GDP, Imidazolide 2'F-GMP, Imidazolide 3'$CF_3$-GDP, Imidazolide m$^7$GMP, 1M tris(triethylammonium) phosphate, and tributylammonium orthophosphate were made as taught herein or in A. Kore, and G. Parmar, *Synthetic Comm.*, 36:3393-3399, 2006, incorporated herein by reference in its entirety.

The cap analogs were analyzed by $^1$H NMR and $^{31}$P NMR (Bruker Avance), 400 MHz. $^1$H was collected at 400.1446006 MHz and the $^{31}$P was collected at 161.9968531, both using a QNP probe. Mass Spectroscopy (i.e., Applied Biosystems/Sciex MDX API 150 model) and MALDI-TOF (Applied Biosystems Voyager DE-PRO model), and analytical HPLC (Aliance, Water's) was performed using Hypersil SAX columns, 5 μm, 250×4.6 mm (Altech).

EXAMPLES

Aspects of the present teachings may be further understood in light of the following examples, which should not be construed as limiting the scope of the present teachings in any way.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Example 1

Synthesis of 7-Methyl Guanosine 5'-diphosphate In a clean, dry 2000 mL round bottom flask equipped with a stirring bar and under a stream of argon slowly dissolve dry and finely powdered guanosine 5'-diphosphate (1), (10.0 g, 20.5 mmol), either in free acid or sodium as a counter ion form, in 200 mL water, adjusting pH to 4.0 with glacial acetic acid. Dimethyl sulfate (20 mL, 119.04 mmol) was then added over a period of one hour with constant stirring at room temperature and the reaction continued for an addition hour during which time a decrease in pH was observed but pH was kept between pH 3.8 to 4.0 by drop-wise addition of 10 mM NaOH and methylations was monitored by analytical HPLC for progress. Methylation was determined to be 98% complete within 2 h. After 2 h, the reaction mixture was extracted with $CHCl_3$(3×200 mL) to remove unreacted excess dimethyl sulfate.

The resulting aqueous layer was further evaporated on a rotary evaporator to remove any chloroform traces, and then further diluted to 1.5 L with water and loaded on an anion exchange resin, i.e., DEAE Sepharosa fast flow packed in a BPG 100 column (Amersham GE, Piscataway, N.J., USA). BPG (biological process glass) 100 specification: 100/500 column (100 mm in diameter and 50 cm in height), packed with DEAF Sepharosa fast flow resin to the bed volume of 400 mm. The desired compound was eluted by using four bed volumes of gradient from 0 to 80% of 1 M TEAB buffer (triethyammonium bicarbonate), pH 7.5, at a flow rate of 100 mL/min, using AKTA purifier 100 FPLC (Amersham GE). At 45% TEAB buffer, 7-methylguanosine 5'-diphosphate (m$^7$GDP) was eluted as a large broad peak, with a strong ultraviolet absorbance at 254 nm. The residual bicarbonate was removed by co-evaporating with methanol, 3×600 mL. The resulting residue was transferred to a centrifuge tube, and 8.9 g sodium perchlorate dissolved in 1.1 L acetone was added and cooled 2 h at 4° C. The resulting mixture was centrifuged and the supernatant liquid was discarded. The precipitate was ground with a new portion of acetone, cooled and centrifuged, repeating once. The precipitate was dried in a vacuum desiccator over $P_2O_5$. The resulting amorphous white powder was 7 methyl-guanosine 5'-diphosphate. Taken from Kore, A. and Parmar, G. *Nucleosides, Nucleotides, and Nucleic Acids,* 25:337-340, 2006, incorporated herein by reference in its entirety.

Example 2

Synthesis of Nucleoside-5'-diphosphates

Although the following procedure illustrates synthesis of guanosine-5'-diphosphate, one of skill in the art would be able to use the procedure for the synthesis of adenosine-5'-diphosphate, uridine-5'-diphosphate, and cytidine-5'-diphosphate and analogs thereof. In a clean, dry 500 mL round bottom flask equipped with a stirring bar the triethylammonium salt of guanosine 5'-monophosphate (10.0 g, 21.5 mmol) in anhydrous dimethylformamide (200 mL) was stirred together, triethylamine was added (2.4 mL, 142.8 mmol) and allowed to stir for 5 min, followed by the addition of Imidazole (5.86 g, 86.1 mmol), 2,2'-dithiodipyridine (7.4 g, 33.58 mmol), and triphenylphosphine (8.9 g, 33.9 mmol). Stirring was continued for 2 h at room temperature. The reaction was allowed to go to completion as determined by HPLC and then poured slowly into a mixture of sodium perchlorate (7 g) in acetone (1500 mL), and then cooled for 30 min. at 4° C. The reaction mixture was centrifuged, discarding the supernatant. Traces of imidazole and triphenylphosphine were removed by grinding the solid with a new portion of acetone (400 mL), cooling and again centrifuged, repeating once. The precipitate was dried in a vacuum oven over $P_2O_5$ at 24° C. (30 mbar pressure). The ribonucleoside-5'-phosphoroimidazolide thus obtained was dissolved in dimethylforamide (200 mL), and a 1 M solution of tributylammonium orthophosphate in dimethylformamide (80 mL) was added drop-wise to the vigorously stirred mixture over a period of 30 min. Zinc chloride (2 g, 14.67 mmol) was added and the reaction mixture stirred at room temperature for 3 h. Completion of the reaction was monitored by HPLC. The reaction mixture was quenched with water (50 mL) and extracted with chloroform (3×200 mL), concentrated in a rotary evaporator and then purified by application to an anion exchange resin.

Purification by column chromatography was accomplished with a DEAE Sepharose fast flow resin packed in an XK 50/60 column (50 mm diameter and 60 cm long) (Amersham GE). The desired compound was eluted by using four bed volumes of gradient from 0 to 80% of 1 M TEAR buffer pH 7.5 (triethylammonium bicarbonate) at a flow rate of 20 mL/min, using an AKTA purifier 100 FPLC (Amersham GE). At 55% TEAB buffer, the desired product (nucleoside-5'-diphosphate) was eluted as a large broad peak, with a strong ultraviolet absorbance at 254 nm. The nucleoside-5'-diphosphate-containing fractions were pooled and evaporated using a rotary evaporator to give triethylamine salt of the desired diphosphate compound. Taken from A. Kore, and G. Parmar, *Synthetic Comm.*, (2006) supra.

Example 3

Synthesis of 3'-O-Methyl Guanosine Monophosphate (3'-O-Me-GMP) TEA Salt (Compound 2)

In a clean, dry 500 mL round bottom flask equipped with a stirring bar and under a stream of argon slowly add dry and finely powdered 3'-O-Me-Guanosine (1), (6 g, 20 mmol) to a mixture of trimethylphosphate ((OMe)$_3$P) (50 mL) and phosphorous oxychloride (POCl$_3$) (6 mL, 60 mmol) at 0° C. in small portions with continuous stirring under argon. The mixture was kept at 0-4° C. and allowed to stir at least 19 hrs. Diethyl ether (200 mL) was added to extract the excess phosphorous oxychloride and to simultaneously precipitate the 3'-O-methylguanosine-5'-phosphodichloridate, which was then pelleted by centrifugation and dissolved in 100 mL icecold 5% NaHCO$_3$ in water. The resulting aqueous solution was adjusted to pH ~1.5 using 1 N NaOH. After stirring at 0-4° C. for an additional 20 h, the pH was adjusted to 7.0 and the resulting mixture was applied to a column of DEAE Sephadex A25. The column was washed with 5 mM TEAB buffer, pH 7.5 and then eluted with freshly prepared 1M Triethylammonium bicarbonate (TEAB) buffer, pH 7.5. Fractions containing the 3'-O-Me GMP TEA salt (2) were pooled, concentrated to dryness.

Example 4

Synthesis of 3'-O-Me-GMP Imidazolide (Compound 3)

In a clean, dry 1 L round bottom flask equipped with a stirring bar and under a stream of argon slowly add anhydrous DMF (144 mL) and the triethylamine (0.933 mL, 9.23 mmol) allow to stir for at least 5 min. To this slowly was add the dry and finely powdered 3'-O-Me-GMP TEA salt (2), (3.5 g, 7.34 mmol) in small portions with continuous stirring under argon. Thereafter the Imidazole (2.05 g, 30.1 mmol), Aldrithiol (2.65 g, 12.02 mmol), and triphenylphosphine (3.13 g, 11.9 mmol) were added and the reaction allowed to stir at room temperature for at least 2-3 h, during which the reactants became soluble making the reaction appear clear yellow colored. Upon completion, sodium perchlorate (3.0 g, 24.5 mmol) dissolved in acetone with continuous stirring and to this mixture, slowly added, was the reaction mixture. This mixture was then poured in two 1 L nalgene bottles and cooled in a refrigerator at −80° C. for 30 minutes. The mixture was then subjected to centrifugation at 3000 rpm for 15 min and the supernatant was discarded. The precipitate was ground with a new portion of acetone and centrifuged. The process was repeated once more and the precipitate was dried in a vacuum desiccator over phosphorous pentoxide, yielding 3'-O-Me-GMP Imidazolide.

Example 5

Synthesis of 3'O-Me-GDP TEA Salt (Compound 4)

Synthesis of Tris(triethylammonium) Phosphate Linker

Anhydrous orthophosphoric acid (22.5 g, 229.59 mmol) was added to 50 mL of anhydrous methylene chloride in a clean, oven dried 250 mL flask equipped with a stirring bar. Tributylamine (54.6 mL, 229.6 mmol) was then added into the solution drop wise through an addition funnel over a period of 30 min. The mixture was left stirring for 1 h. CH$_2$Cl$_2$ was then evaporated and the reaction residue was co-evaporated with 3×30 mL of anhydrous pyridine and then 2×30 mL of anhydrous DMF. The Tris(triethylammonium) phosphate linker product was dissolved in 100 mL anhydrous DMF so as to have a final concentration of 1 M, and stored over 4 Å molecular sieves at 4° C.

In a clean, dry 1 L round bottom flask equipped with a stirring bar and under a stream of argon anhydrous DMF (40 mL) was slowly added and stirred for at least 5 minutes. To this was slowly added finely powdered 3'-O-Me-GMP Imidazolide (3), (3.0 g, 7.04 mmol) in small portions with continuous stirring under argon. Zinc chloride (2.0 g, 14.6 7 mmol) was added in small portions until the contents were dissolved. Thereafter, the tris(triethylammonium) phosphate linker and 1 M tributylammonium orthophosphate (40 mL) was added slowly to the reaction mixture under argon and the reaction was allowed to stir at room temperature for 5 h. The reaction when followed on HPLC showing complete conversion of the starting material, 3'-O-Me-GMP Imidazolide (3) to its corresponding diphosphate. Upon completion, the reaction was supplemented with water, 100 mL, and the resultant mixture was extracted with chloroform (3×250 mL), subjected to volume reduction (~100 mL) by evaporation and applied to DEAE Sephadex A25 column, eluting with a linear gradient of freshly prepared 1 M TEAB, pH 7.5. The fractions containing the pure 3'-O-Me-GDP TEA salt (compound 4) were eluted, combined and evaporated to dryness.

Example 6

Synthesis of m$_2^{7,3'O}$ GDP (Compound 5)

To a stirred solution of 3'-O-Me-GDP TEA salt (4), (4.0 g, 6.1 mmol) in 100 mL of nuclease free water, concentrated glacial acetic acid was slowly added to adjust the pH of the solution to 4.0; dimethyl sulfate ((Me)$_2$SO$_4$) (20 mL, 210 mmol) was slowly added drop wise over a period of 60 min, while maintaining the pH~4.0-4.5 with 50 mM NaOH. The reaction was allowed to stir at room temperature for 2 h and methylation was monitored by HPLC. After 2 h, the reaction mixture was extracted with CHCl$_3$ (3×250 mL) to remove unreacted dimethyl sulfate. The aqueous layer was applied to a DEAE Sephadex column and the fractions containing the product were pooled, evaporated and dried in a vacuum desiccator over phosphorous pentoxide to give 3'-O-Me (N$^7$-Me) GDP (compound 5) as a fine powder.

Example 7

Synthesis of m$_2^{7,3'O}$G[5']ppp[5']G (Compound 7)

In a clean, dry 1 L round bottom flask equipped with a stirring bar and under a stream of argon anhydrous DMF (165 mL) was slowly added and allowed to stir. To this was slowly add finely powdered 3'-O-Me-GDP TEA salt (5), (4.0 g, 5.84 mmol) in small portions with continuous stirring under argon. Zinc chloride (2.0 g, 14.67 mmol) was added in small portions until the contents were dissolved. Thereafter, the Imidazolide GMP (compound 6) (6.00 g, 14.08 mmol) was slowly added to the reaction mixture under argon. The reaction was allowed to stir at room temperature and methylation was monitored by HPLC. Upon complete disappearance of starting material, 3'-O-Me-GDP TEA salt, the reaction was poured into a solution of EDTA (3.0 g) in water (200 mL) and pH adjusted to 7.0 with saturated NaHCO$_3$. This was then applied to a DEAE Sephadex column, eluted with a linear gradient of freshly prepared 1 M TEAB, pH 7.5 and the fractions containing the product were pooled, evaporated and dried to give pure 3'-O-Me-N7-Me-G[5']ppp[5']G (compound 7), stored at −20° C.

Example 8

Synthesis of m$_2^{7,3'O}$G[5']ppp[5']m$^7$G (Compound 8)

To a stirred solution of compound 7 (500 mg, 0.612 mmol) in 5.0 mL water, concentrated glacial acetic acid was added slowly to adjust the pH of the solution to 4.0 and to this mixture dimethyl sulfate (2.0 mL, 21.1 mmol) was slowly added drop-wise over a period of 60 min, while maintaining the at pH~4.0-4.5 with 50 mM NaOH. The reaction was allowed to stir at room temperature for 2 h and methylation was monitored by HPLC. After 2 h, the reaction mixture was extracted with CHCl3 (3×50 mL) to remove unreacted dimethyl sulfate. The aqueous layer was applied to a DEAE Sephadex column and the fractions containing the product were pooled, evaporated and dried to give pure trimethylated CAP (m27,3'OG[5']ppp[5']m7G) (compound 8) which was then passed through a Strata AW column to remove the salt and make it a free acid form.

Example 9

Synthesis of 2'F GMP (Compound 14)

To a stirred solution of POCl$_3$ (3.97 g, 26.3 mmol) and (OMe)$_3$P (20.0 mL) at 0° C. under nitrogen atmosphere, T-fluro guanosine (2.5 g, 8.77 mmol) was added and the reaction mixture was stirred for 2 h at 0° C. After 2 h, 50.0 mL water was added to the reaction mixture. The resulting reaction mixture was washed with ethyl acetate (2×50 mL) to remove the phosphorylating agent. The collected aqueous solution was adjusted to pH 1.5 drop-wise with IN NaOH and allowed to stir at 4° C. for 12 h. After 12 h, the aqueous solution was concentrated under a rotor evaporator to around 20 mL. To a solution of sodium perchlorate (3.0 g) in 100 mL acetone in a centrifuge tube at 0° C. this concentrated solution (20.0 mL) was added slowly for 2 minutes. The resulting mixture was centrifuged and the supernatant liquid was removed. This precipitate was dissolved in 500 mL water and adjusted the pH to 5.5 with saturated NaHCO$_3$ and loaded on a DEAE Sephadex column. The desired product was eluted using a linear gradient of 0-1M TEAB buffer, pH 7.5 and the fractions containing the product were pooled, evaporated and dried in a vacuum desiccator over phosphorous pentoxide (P$_2$O$_5$) to give 2P GMP as a fine white powder (compound 14) (Yield: 3.54 g, 87%).

Example 10

Synthesis of Imidazolide 2'F GMP (Im2'T GMP) (Compound 15)

To a stirred solution of 2'F GMP TEA salt 14 (2.0 g, 4.3 mmol) in a 50 mL dry DMF, imidazole (1.50 g, 21.5 mmol), triphenyl phosphine (PPh$_3$) (2.26 g, 8.6 mmol), aldrithiol (1.90 g, 8.6 mmol) and triethylamine (0.43 g, 4.3 mmol) were added. The reaction mixture was stirred under nitrogen atmosphere at room temperature for 5 h. To a solution of sodium perchlorate (2.0 g) in 100 mL acetone in a centrifuge tube at 0° C., the above reaction mixture was added slowly for 5 minutes. The resulting mixture was centrifuged and the supernatant liquid was removed. The solid was ground with a new portion of acetone (100 mL), cooled, and centrifuged again. This process was repeated twice, and the resulting solid was dried in a vacuum desiccator over P$_2$O$_5$ to give Imidazolide 2'F GMP as a white powder (compound 15) (Yield: 1.44 g, 81%).

Example 11

Synthesis of 2'F GDP (Compound 16)

To a stirred solution of Imidazolide 2'F GMP 15 (1.2 g, 2.89 mmol) and Zinc chloride (0.38 g, 2.89 mmol) in 10.0 mL dry DMF, 18 mL of 1M tris(triethylammonium) phosphate (tris (Et$_3$NH)$_3$PO$_4$) in DMF was added under nitrogen atmosphere. The reaction mixture was stirred at room temperature for 3 h. After 3 h, the reaction mixture was diluted with 50.0 mL of water. The resulting reaction mixture was washed with ethyl acetate (2×50 mL) to remove the phosphorylating agent. The collected aqueous solution was adjusted to pH 5.5 with saturated NaHCO$_3$ and loaded on a DEAE Sephadex column. The desired product was eluted using a linear gradient of 0-1M TEAB buffer, pH 7.5 and the fractions containing the product were pooled, evaporated and dried in vacuum desiccator over phosphorous pentoxide to give 2'F GDP as a fine white powder (compound 16) (Yield 1.34 g, 72%).

Example 12

Synthesis of m$^{7,2'F}$ GDP (Compound 17)

To a stirred solution of 2'F GDP 16 (0.75 g, 1.16 mmol) in 20.0 mL of water, acetic acid was added slowly to adjust the pH of the solution to 4.0. To this mixture, dimethyl sulfate (3.0 mL) was added drop-wise over a period of 30 min. and the reaction mixture was allowed to stir at room temperature for 4 h. As the methylation proceeds, the pH decreased to around pH 2.0 and was re-adjusted back to pH 4.0 using a 1M NaOH solution. After 4 h, the reaction mixture was extracted with CHCl3 (3×50 mL) to remove unreacted, excess dimethyl sulfate. The collected aqueous solution was adjusted to pH 5.5 with saturated NaHCO$_3$ and applied onto a DEAE Sephadex column. The final product was monitored for methylation by HPLC and eluted using a linear gradient of 0-1M TEAS buffer, pH 7.5 and the fractions containing the product were pooled, evaporated and dried in vacuum desiccator over phosphorous pentoxide to give m$^{7,2'F}$ GDP as a fine white powder (compound 17) (Yield 0.64 g, 83%).

Example 13

Synthesis of m$^{7,2'F}$GpppG (Compound 18)

To a stirred solution of m$^{7,2'F}$GDP 17 (0.2 g, 0.3 mmol) and Imidazolide GMP (ImGMP) (0.19 g, 0.45 mmol) in 10.0 mL dry DMF, Zinc chloride (81 mg, 0.6 mmol) was added under nitrogen atmosphere and the reaction mixture was stirred at room temperature for 1 h. After 1 h, the reaction mixture was added to a solution of EDTA disodium (0.45 g, 1.2 mmol) in 100.0 mL of water at 0° C. The resulting aqueous solution was adjusted to pH 5.5 with saturated NaHCO$_3$ and loaded on a DEAE Sephadex column. The desired product was eluted using a linear gradient of 0-1M TEAB buffer, pH 7.5 and the fractions containing the product were pooled, evaporated and concentrated to 10.0 mL TEA salt of compound 18. The resulting 10.0 mL was passed through a Strata-X-AW column and washed with 10.0 mL water followed by 10.0 mL MeOH. Then, compound 18 was eluted with 15.0 mL of NH$_4$OH/MeOH/H$_2$O (2/25/73) and the collected solution was evaporated and dried to give m$^{7,2'F}$GpppG as a fine white powder (compound 18) (Yield: 0.15 g, 58%).

HPLC Analysis: The starting imidzaolide gave a peak at 3.49 min. and the GDP peak was at 5.95 min. The new product peak was at 7.13 min. The crude reaction mixture after 1 h gave 97% of the product peak (7.14 min.) and 3% of the starting material peak (5.95 min.).

Data for 18. $^1$H NMR (D$_2$O, 400 MHz) δ 8.02 (s, 1H), 6.14 (d, J=14.4 Hz, 1H), 5.80 (d, J=5.6 Hz, 1H), 5.41-5.27 (m, 1H), 4.63-4.47 (m, 3H), 4.39-4.24 (m, 6H), 4.03 (s, 3H); $^{31}$P NMR (D$_2$O, 162 MHz) δ-10.4 (d, J=16.8 Hz), -10.54 (d, J=18.6 Hz), -21.95 (t, J=19.3 Hz); $^{19}$F NMR (D$_2$O, 376 MHz) δ-20.47 (m); MS (m/z): 803 [M+H]$^+$.

Example 14

Synthesis of m$^{7,2'-F}$G[5']ppp[5]m$^7$G (Compound 20)

To a stirred solution of m$^{7,2'F}$GDP 17 (0.25 g, 0.38 mmol) and Imidazolide m$^7$GMP (m$^7$-ImGMP) (0.24 g, 0.57 mmol) in 10.0 mL dry DMF, Zinc chloride (0.10 g, 0.76 mmol) was added under nitrogen atmosphere and the reaction mixture was stirred at room temperature for 6 h. After 6 h, the reaction mixture was added to a solution of EDTA disodium (0.57 g, 1.52 mmol) in 100.0 mL of water at 0° C. The resulting aqueous solution was adjusted to pH 5.5 with saturated NaHCO$_3$ and loaded on a DEAE Sephadex column.

The desired product was eluted using a linear gradient of 0-1M TEAB buffer, pH 7.5 and the fractions containing the product were pooled, evaporated and concentrated to 10.0 mL TEA salt of compound 20. The resulting 10.0 mL was passed through a Strata-X-AW column and washed with 10.0 mL water followed by 10.0 mL, MeOH. Then, compound 20 was eluted with 15.0 mL of NH$_4$OH/MeOH/H$_2$O (2/25/73) and the collected solution was evaporated and dried to give m$^{7,2'-F}$Gpppm$^7$G as a fine white powder (compound 20) (Yield: 0.21 g, 64%).

Data for 20: $^1$H NMR (D$_2$O, 400 MHz) δ 6.31 (d, J=14.8 Hz, 1H), 6.02 (d, J=3.2 Hz, 1H), 5.53-5.37 (m, 1H), 4.75-4.62 (m, 2H), 4.52-4.38 (m, 5H), 4.30-4.21 (m, 2H), 4.11 (s, 6H);

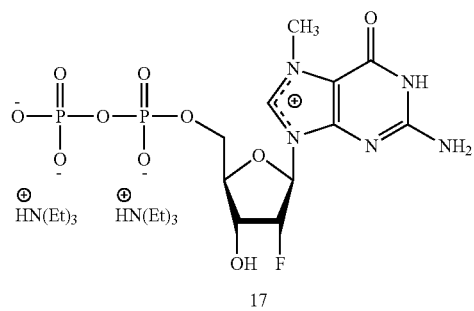

17

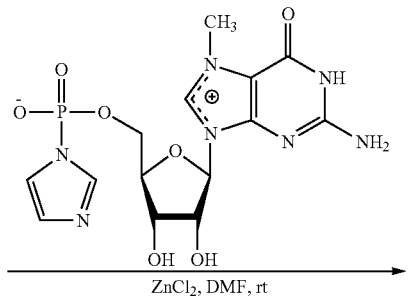

ZnCl$_2$, DMF, rt

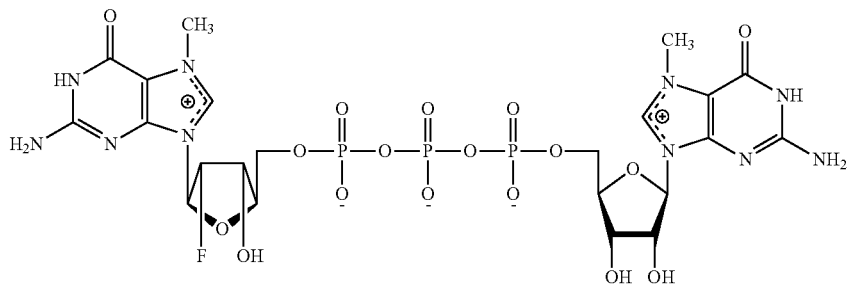

20

$^{31}$P NMR (D$_2$O, 162 MHz) δ-10.35 (d, J=11.8 Hz), -10.50 (d, J=10.0 Hz), -21.80 (t, J=19.1 Hz); $^{19}$F NMR (D$_2$O, 376 MHz) δ-20.51 (m); MS (m/z): 817 [M]$^+$.

Example 15

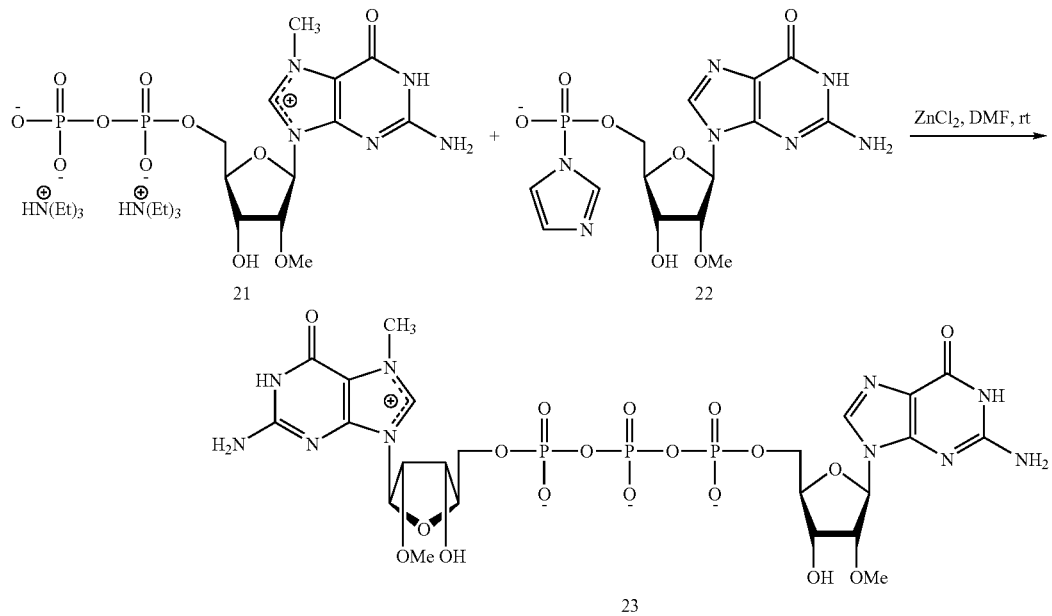

Synthesis of m$_2^{7,2'O}$G[5']ppp[5']m$^{2'O}$G (Compound 23)

To a stirred solution of m$_2^{7,2'O}$GDP (N7Me2'O-MeGDP) 21 (0.22 g, 0.33 mmol) and Imidazolide m$^{2'O}$[GMP (Im2'O-MeGMP) 22 (0.14 g, 0.33 mmol) in 10.0 mL dry DMF, Zinc chloride (0.09 g, 0.66 mmol) was added under nitrogen atmosphere and the reaction mixture was stirred at room temperature for 2 h. After 2 h, the reaction mixture was added to a solution of EDTA disodium (0.49 g, 1.32 mmol) in 100.0 mL of water at 0° C. The resulting aqueous solution was adjusted to pH 5.5 with saturated NaHCO$_3$ and loaded on a DEAE Sephadex column. The desired product was eluted using a linear gradient of 0-1M TEAB buffer, pH 7.5 and the fractions containing the product were pooled, evaporated and concentrated to 10.0 mL TEA salt of compound 23. The resulting 10.0 mL was passed through a Strata-X-AW column and washed with 10.0 mL water followed by 10.0 mL MeOH. Then, compound 23 was eluted with 15.0 mL of NH$_4$OH/MeOH/H$_2$O (2/25/73) and the collected solution was evaporated and dried to give m$_2^{7,2'O}$G[5']ppp[5']m$^{2'O}$G as a fine white powder (compound 23) (Yield: 0.18 g, 63%).

Data for 23: NMR (D$_2$O, 400 MHz) δ 8.00 (s, 2H), 5.90 (d, J=2.0 Hz, 1H), 5.83 (d, J=5.2 Hz, 1H), 4.59 (t, J=4.4 Hz, 1H), 4.53-4.41 (m, 2H), 4.33-4.22 (m, 6H), 4.16 (m, 1H), 4.06 (s, 3H), 3.60 (s, 3H), 3.45 (s, 3H); $^{31}$P NMR (D$_2$O, 162 MHz) δ-10.35 (t, J=17.8 Hz), -21.83 (t, J=18.0 Hz); MS (m/z): 831 [M]$^+$.

Example 16

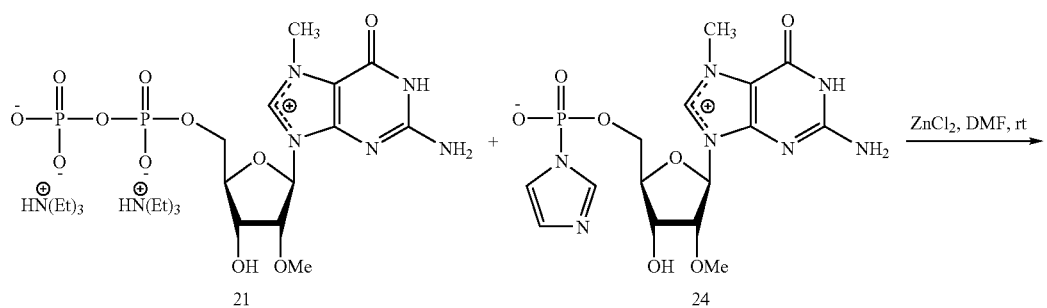

-continued

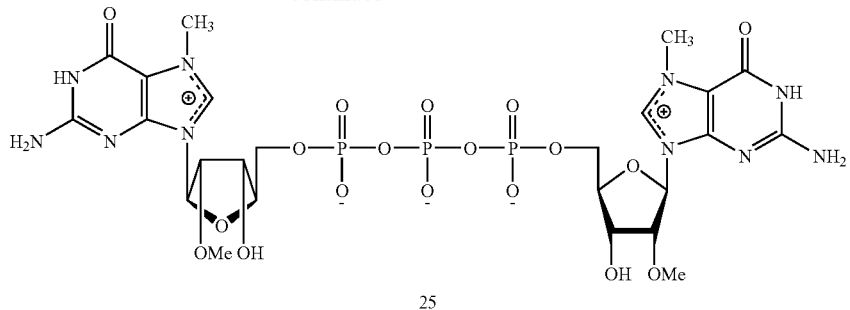

25

Synthesis of $m_2^{7,2'O}G[5']ppp[5']m_2^{7,2'O}G$ (Compound 25)

To a stirred solution of $m_2^{7,2'O}$GDP (N7Me2'-O-MeGDP) 21 (0.18 g, 0.27 mmol) and Imidazolide $m_2^{7,2'O}$GMP (Im N7Me-2'-O-MeGMP) 24 (0.18 g, 0.41 mmol) in 10.0 mL dry DMF, Zinc chloride (0.07 g, 0.54 mmol) was added under nitrogen atmosphere and the reaction mixture was stirred at room temperature for 6 h. After 6 h, the reaction mixture was added to a solution of EDTA disodium (0.40 g, 1.08 mmol) in 100.0 mL of water at 0° C. The resulting aqueous solution was adjusted to pH 5.5 with saturated $NaHCO_3$ and loaded on a DEAE Sephadex column. The desired product was eluted using a linear gradient of 0-1M TEAB buffer, pH 7.5 and the fractions containing the product were pooled, evaporated and concentrated to 10.0 mL TEA salt of compound 25. The resulting 10.0 mL was passed through a Strata-X-AW column and washed with 10.0 mL water followed by 10.0 mL MeOH. Then, compound 25 was eluted with 15.0 mL of $NH_4OH$/ MeOH/$H_2O$ (2/25/73) and the collected solution was evaporated and dried to give $m_2^{7,2'O}G[5']ppp[5']m_2^{7,2'O}G$ as a fine white powder (compound 25) (Yield: 0.13 g Data for 25: $^1H$ NMR ($D_2O$, 400 MHz) δ 6.10 (d, J=2.8 Hz, 2H), 4.59 (t, J=5.2 Hz, 2H), 4.43-4.23 (m, 8H), 4.11 (s, 6H), 3.61 (s, 6H); $^{31}P$ NMR ($D_2O$, 162 MHz) δ −10.32 (d, J=18.1 Hz), −21.72 (t, J=20.7 Hz); MS (m/z): 845 $[M-H]^+$.

Example 17

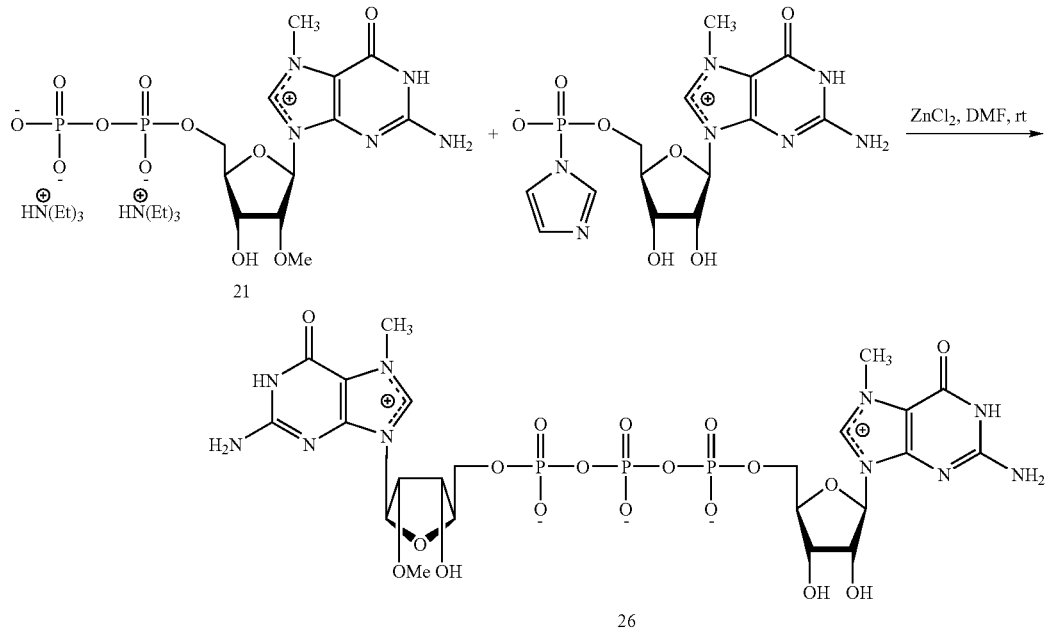

26

Synthesis of $m_2^{7,2'O}G[5']ppp[5']m^7G$ (Compound 26)

To a stirred solution of $m_2^{7,2'O}$ GDP (N7Me2'-O-MeGDP) 21 (0.20 g, 0.3 mmol) and Imidazolide $m^7$ GMP (Im$N^7$MeGMP) (0.19 g, 0.45 mmol) in 10.0 mL dry DMF, Zinc chloride (0.08 g, 0.6 mmol) was added under nitrogen atmosphere and the reaction mixture was stirred at room temperature for 6 h. After 6 h, the reaction mixture was added to a solution of EDTA disodium (0.45 g, 1.2 mmol) in 100.0 mL of water at 0° C. The resulting aqueous solution was adjusted to pH 5.5 with saturated $NaHCO_3$ and loaded on a DEAE Sephadex column. The desired product was eluted using a linear gradient of 0-1M TEAB buffer, pH 7.5 and the fractions containing the product were pooled, evaporated and concentrated to 10.0 mL TEA salt of 26. The resulting 10.0 mL was passed through a Strata-X-AW column and washed with 10.0 mL water followed by 10.0 mL MeOH. Then, compound 26 was eluted with 15.0 mL of $NH_4OH$/MeOH/

H₂O (Feb. 25, 1973) and the collected solution was evaporated and dried to give a fine white powder (compound 26) (Yield: 0.16 g, 62%)

Data for 26: $^1$H NMR (D$_2$O, 400 MHz) δ 6.10 (d, J=2.8 Hz, 1H), 6.01 (d, J=3.6 Hz, 1H), 4.63 (t, J=5.6 Hz, 1H), 4.58 (t, J=5.6 Hz, 1H), 4.49 (t, J=5.6 Hz, 1H), 4.41-4.31 (m, 5H), 4.27-4.23 (m, 2H), 4.12 (s, 6H), 3.60 (s, 3H); $^{31}$P NMR (D$_2$O, 162 MHz) δ-10.36 (d, J=19.0 Hz), −21.77 (t, J=19.3 Hz); MS (m/z): 829 [M]$^+$.

Example 18

T7 RNA Transcription

T7 RNA polymerase transcription was performed by using mMESSAGE mMACHINE® T7 Kit (Ambion) in 20 μL final volume, and contains the following reagents at the final concentrations indicated: 1 μg linearized AmbLuc PolyA DNA, 1× reaction buffer, 7.5 mM of each ATP, UTP, and CTP, 1.5 mM GTP, 6.5 mM of mCAP and 2' fluoro cap analogs, and 50 U/μl of T7 RNA polymerase. The transcription reactions were incubated at 37° C. for 2 hours. In order to hydrolyze the remaining plasmid DNA, 1 μL of turbo DNAse was added to the reaction mixture, and further incubated at 37° C. for 15 minutes. The transcribed capped and uncapped mRNAs were purified by using the MEGAclear™ Kit (Ambion).

AmbLuc Poly(A) (Ambion), transcription produced comparable yields for modified and standard cap analogs (see FIGS. 5 and 6). The Bioanalyzer assay indicates that all the mRNAs are not degraded and retain great integrity (see FIG. 7).

Example 19

Translation Assay

Protein expression from mCAP, double methylated, triple methylated, and ARCA capped luciferase RNAs, at different time points after transfection with HeLa cells indicates that the transcripts containing triple methylated cap are more highly translated in transfected cells. Comparison of protein expression with mCAP and double methylated cap suggest that the double methylated cap transcript produces one fold higher protein, while ARCA produces 3 fold higher, and triple methylated cap produces 4 fold higher protein in in vivo with HeLa cells. See FIG. 9.

All modified cap compounds tested are substrates for T7 polymerase, as determined by gel shift assays that clearly revealed that capped RNAs were formed, based on slower migration relative to uncapped RNAs (see FIGS. 8 and 10).

The examples above described particular cap analogs, however, there are additional cap analogs conceived which will also function in practicing the invention as illustrated below:

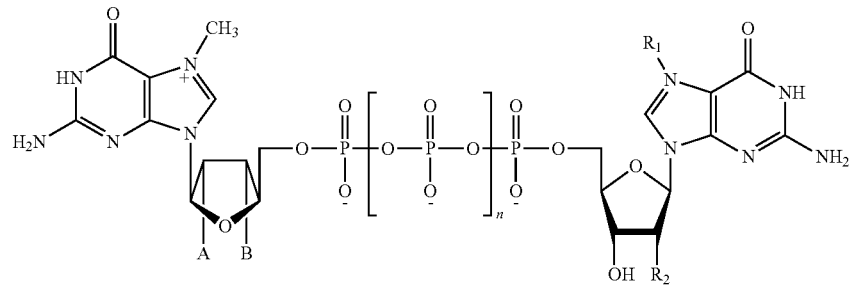

General Structure of CAP

| No. | Abbreviation | A(2') | B (3') | R$_2$ (2') | R$_1$ |
|---|---|---|---|---|---|
| A | m$^{7,2'F}$G[5']ppp[5']$^{2F}$G | F | OH | F | — |
| B | m$^{7,2'F}$G[5']ppp[5']$^{7,2'F}$G | F | OH | F | CH$_3$ |
| C | m$^{7,3'CF_3}$G[5']ppp[5']G | OH | CF$_3$ | OH | — |
| D | m$^{7,3'CF_3}$G[5']ppp[5']m$^7$G | OH | CF$_3$ | OH | CH$_3$ |
| E | m$^{7,3'NH_2}$G[5']ppp[5']$^{2F}$G | OH | NH$_2$ | F | — |
| F | m$^{7,3'NH_2}$G[5']ppp[5']$^{7,2'F}$G | OH | NH$_2$ | F | CH$_3$ |
| G | m$^{7,3'NO_2}$G[5']ppp[5']G | OH | NO$_2$ | OH | — |
| H | m$^{7,3'NO_3}$G[5']ppp[5']m$^7$G | OH | NO$_2$ | OH | CH$_3$ |
| I | m$^{7,3'NH_2}$G[5']ppp[5']G | OH | NH$_2$ | OH | — |
| J | m$^{7,3'NH_2}$G[5']ppp[5']m$^7$G | OH | NH$_2$ | OH | CH$_3$ |
| K | m$^{7,3'NH_2}$2'dG[5']ppp[5']G | deoxy | NH$_2$ | OH | — |
| L | m$^{7,3'NH_2}$2'dG[5']ppp[5']m$^7$G | deoxy | NH$_2$ | OH | CH$_3$ |
| M | m$^{7,3'NH_2}$2'dG[5']ppp[5']$^{2F}$G | deoxy | NH$_2$ | F | — |
| N | m$^{7,3'NH_2}$2'dG[5']ppp[5']m$^{7,2'F}$G | deoxy | NH$_2$ | F | CH$_3$ |
| O | m$^{7,3'N_3}$G[5']ppp[5']G | OH | N$_3$ | OH | — |
| P | m$^{7,3'N_3}$G[5']ppp[5']m$^7$G | OH | N$_3$ | OH | CH$_3$ |
| Q | m$^{7,3'N_3}$2'dG[5']ppp[5']G | deoxy | N$_3$ | OH | — |
| R | m$^{7,3'N_3}$2'dG[5']ppp[5']m$^7$G | deoxy | N$_3$ | OH | CH$_3$ |
| S | m$_2^{7,3'O}$G[5']ppp[5']m$^{2'O}$G | OH | OMe | OMe | — |
| T | m$_2^{7,3'O}$G[5']ppp[5']m$_2^{7,3'O}$G | OH | OMe | OMe | CH$_3$ |
| U | m$^{7,3'CHO}$G[5']ppp[5']G | OH | CHO | OH | — |
| V | m$^{7,3'CHO}$G[5']ppp[5']m$^7$G | OH | CHO | OH | CH$_3$ |
| W | m$_2^{7,3'O}$G[5']ppp[5']$^{2F}$G | OH | OMe | F | — |
| X | m$_2^{7,3'O}$G[5']ppp[5']m$^{7,3'F}$G | OH | OMe | F | CH$_3$ |
| Y | m$^{7,3'F}$2'dG[5']ppp[5']G | deoxy | F | OH | — |
| Z | m$^{7,3'S}$2'dG[5']ppp[5']G | deoxy | S | OH | — |
| Aa | m$^{7,3'TBDMS}$G[5']ppp[5']G | OH | TBDMS | OH | — |

-continued

General Structure of CAP

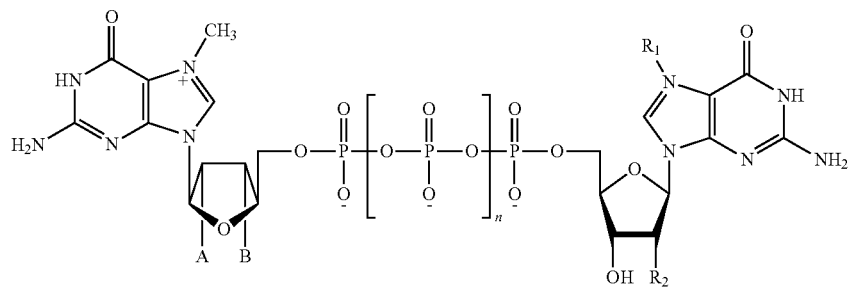

| No. | Abbreviation | A(2') | B (3') | $R_2$ (2') | $R_1$ |
|---|---|---|---|---|---|
| Bb | $m^{7,2'TBDMS}G[5']ppp[5']G$ | TBDMSD | OH | OH | — |
| Cc | $m^{7,LNA}G[5']pppp[5']G$ | OH | LNA | OH | — |
| Dd | $m^{7,LNA}G[5']pppp[5']m^7G$ | OH | LNA | OH | $CH_3$ |
| Ee | $m^{7,2'3'Isopropylidine}G[5']pppp[5']G$ | 2',3'-O-Iso-propylidene | 2',3'-O-Iso-propylidene | OH | — |
| Ff | $m^{7,2'3'Isopropylidine}G[5']pppp[5']m^7G$ | 2',3'-O-Iso-propylidene | 2',3'-O-Iso-propylidene | OH | $CH_3$ |

Example 20

Scheme to Make $m^{7,2'F}G[5']ppp[5']^{2'F}G$ and $m^{7,2'F}G[5']ppp[5']m^{7,2'F}G$

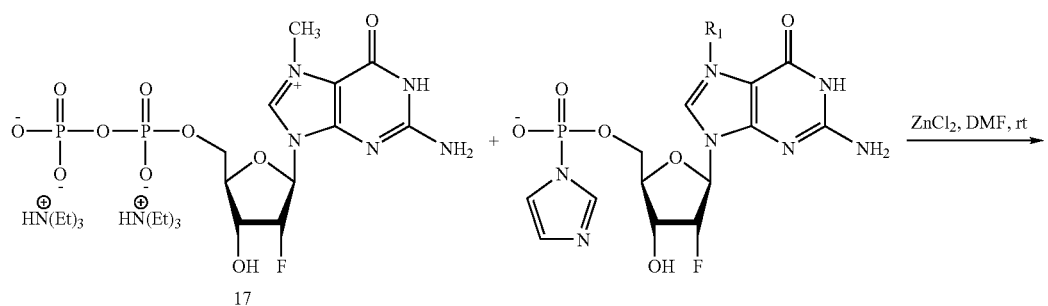

17

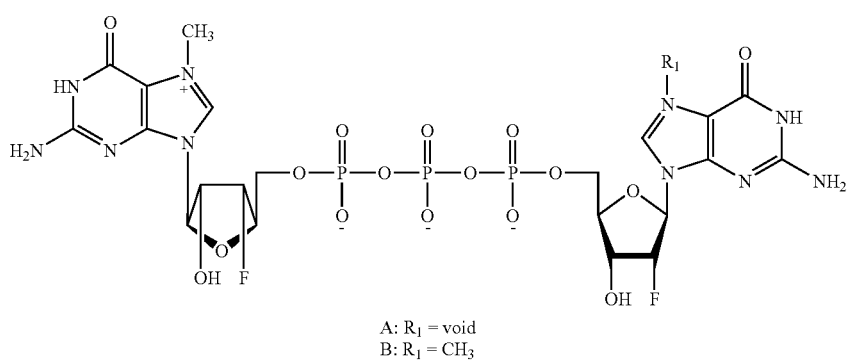

A: $R_1$ = void
B: $R_1$ = $CH_3$

The coupling reaction of $m^{7,2'F}GDP$ (N7Me-2'FGDP) with Imidazolide $^{2'F}GMP$ (Im2'FGMP), or Imidazolide $m^{7,2'F}GMP$ (N7MeIm2'FGMP) in the present of $ZnCl_2$ as the catalyst affords the corresponding cap analogs A and B.

Example 21

Scheme to Make $m^{7,3'NH_2}G[5']ppp[5']^{2'F}G$ and $m^{7,3'NH_2}G[5']ppp[5']m^{7,2'F}G$ The coupling reaction of $m^{7,3'NH_2}GDP$ (N7Me-3'NH$_2$GDP) with Imidazolide $^{2'F}GMP$ (Im2'FGMP), or Imidazolide $m^{7,2'F}GMP$ (N7MeIm2'FGMP) in the presence of ZnCl$_2$ as the catalyst affords the corresponding cap analogs E and F.

Example 22

Scheme to Make $m^{7,3'NH_2}2'dG[5']ppp[5']G$, $m^{7,3'NH_2}2'dG[5']ppp[5']m^7G$, $m^{7,3'NH_2}2'dG[5']ppp[5']^{2'F}G$, and $m^{7,3'NH_2}2'dG[5']ppp[5']m^{7,2'F}G$

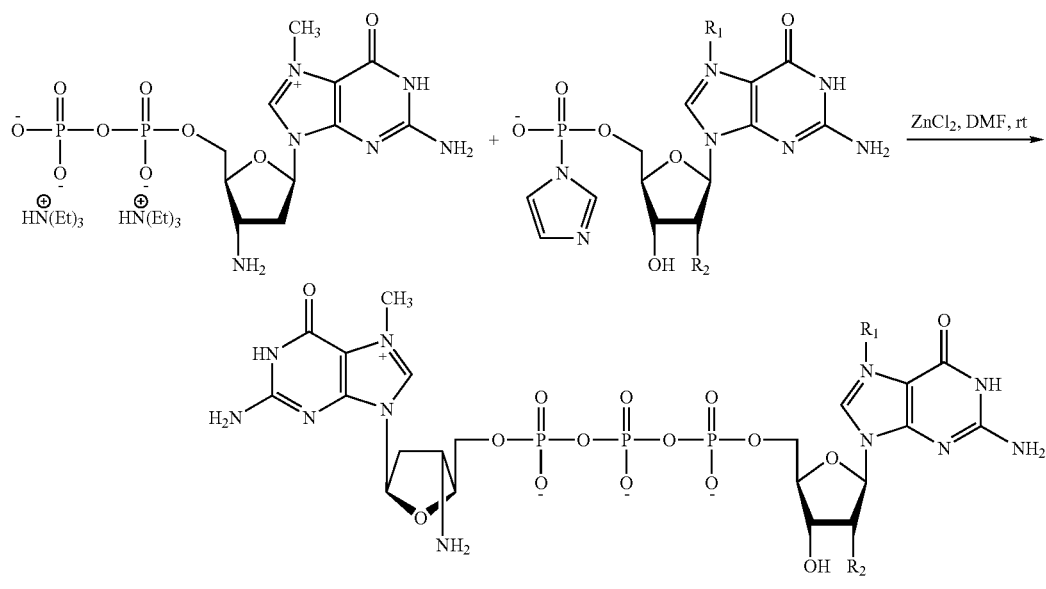

K: R$_1$ = void, R$_2$ = OH
L: R$_1$ = CH$_3$, R$_2$ = OH
M: R$_1$ = void, R$_2$ = F
N: R$_1$ = CH$_3$, R$_2$ = F The coupling reaction of $m^{7,3'NH_2}2'dGDP$ (N7Me-3'NH$_2$2'dGDP) with the corresponding substituted Imidazolide GMP (ImGMP), Imidazolide $m^7$GMP (m7-ImGMP), Imidazolide GMP (Im2'FGMP), or Imidazolide $m^{7,2''F}$GMP (N7MeIm2'FGMP), respectively, in the presence of ZnCl$_2$ as the catalyst affords the corresponding cap analogs K, L, M, and N.

Scheme to Make C, D, G, H, I, J, O, P, Q, and R:

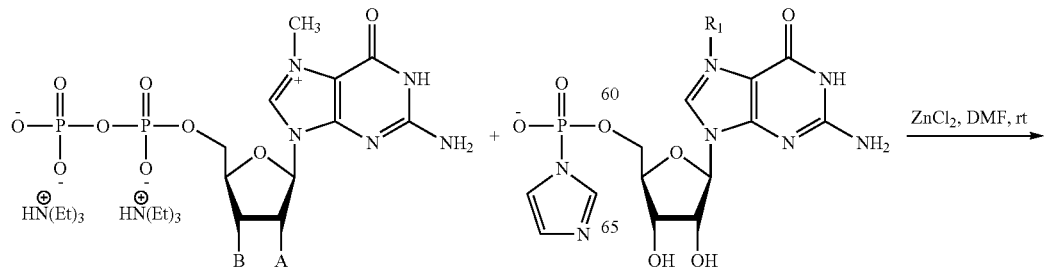

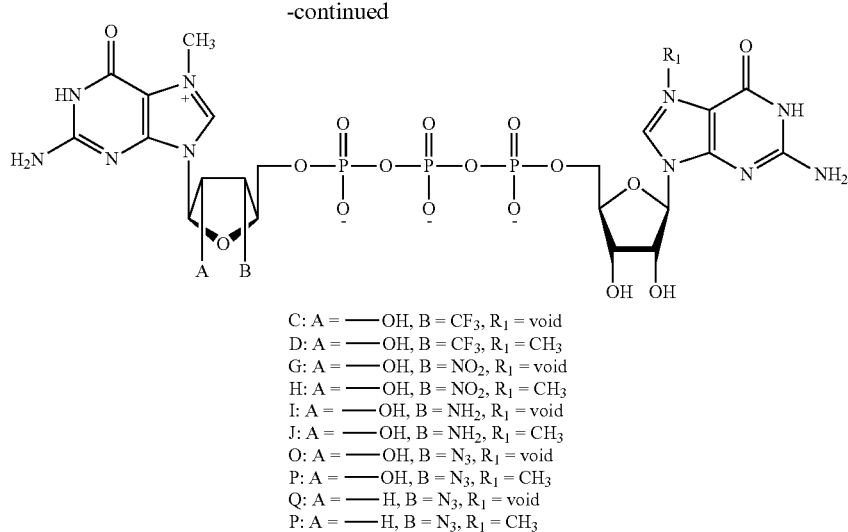

C: A = ——OH, B = CF₃, R₁ = void
D: A = ——OH, B = CF₃, R₁ = CH₃
G: A = ——OH, B = NO₂, R₁ = void
H: A = ——OH, B = NO₂, R₁ = CH₃
I: A = ——OH, B = NH₂, R₁ = void
J: A = ——OH, B = NH₂, R₁ = CH₃
O: A = ——OH, B = N₃, R₁ = void
P: A = ——OH, B = N₃, R₁ = CH₃
Q: A = ——H, B = N₃, R₁ = void
P: A = ——H, B = N₃, R₁ = CH₃

Example 23

Scheme to Make $m^{7,3'CF_3}G[5']ppp[5']G$ and $m^{7,3'CF_3}G[5']ppp[5']m^7G$

The coupling reaction of $m^{7,3'CF_3}GDP$ (N7Me-3'CF₃GDP) with Imidazolide GMP (ImGMP) or Imidazolide $m^7$GMP ($m^7$-ImGMP) in the presence of ZnCl₂ as the catalyst affords the corresponding cap analogs C and D.

Example 24

Scheme to Make $m^{7,3'NO_2}G[5']ppp[5']G$, $m^{7,3'NO_2}G[5']ppp[5']m^7G$, $m^{7,3'NH_2}G[5']ppp[5']G$, and $m^{7,3'NH_2}G[5']ppp[5']m^7G$ The coupling reaction of $m^{7,3'NO_2}GDP$ (N7Me-3'NO₂GDP) or $m^{7,3'NH_2}GDP$ (N7Me-3'NH₃GDP) with Imidazolide GMP (ImGMP) or Imidazolide $m^7$GMP ($m^7$-ImGMP) in the presence of ZnCl₂ as the catalyst affords the corresponding cap analogs G, H, I, and J.

Example 25

Scheme to Make $m^{7,3'N_3}G[5']ppp[5']G$ and $m^{7,3'N_3}G[5']ppp[5']m^7G$

The coupling reaction of $m^{7,3'N_3}GDP$ (N7Me-3'N₃GDP) with Imidazolide GMP (ImGMP) or Imidazolide $m^7$GMP ($m^7$-ImGMP) in the presence of ZnCl₂ as the catalyst affords the corresponding cap analogs O and P.

Example 26

Scheme to Make $m^{7,3'N_3}2'dG[5']ppp[5']G$ and $m^{7,3'N_3}2'dG[5']ppp[5']m^7G$ The coupling reaction of $m^{7,3'N_3}2'dGDP$ (N7Me-3'N₃2'dGDP) with Imidazolide GMP (ImGMP) or Imidazolide $m^7$GMP (m7-ImGMP) in the presence of ZnCl₂ as the catalyst affords the corresponding cap analogs Q and R.

Example 27

Scheme to Make $m_2^{7,3'O}G[5']ppp[5']m^{2'O}G$ and $m_2^{7,3'O}G[5']ppp[5']m_2^{7,2'O}G$

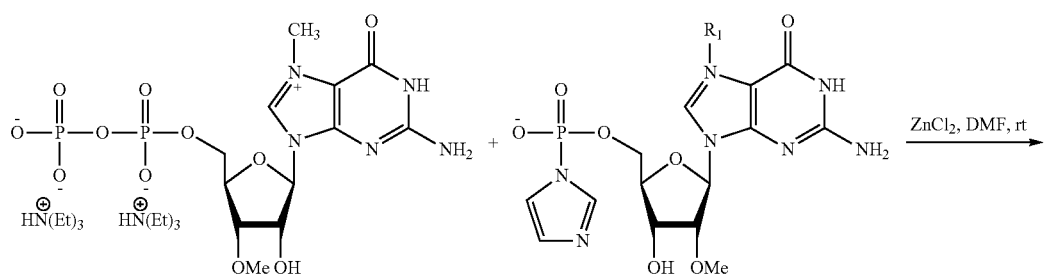

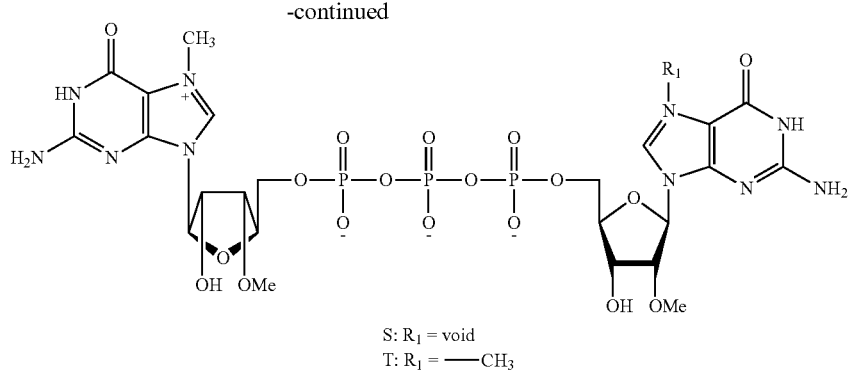

S: R₁ = void
T: R₁ = —CH₃

The coupling reaction of $m_2^{7,3'O}$GDP (N7Me-3'OMe-GDP) with Imidazolide $m^{2'O}$GMP ($Imm^{2'O}$GMP) or Imidazolide $m_{2,7'O}$GMP (N7Me-2'OMeImGMP) presence of $ZnCl_2$ as the catalyst affords the corresponding cap analogs S and T.

Example 28

Scheme to Make $m^{7,3'CHO}$G[5']ppp[5']G and $m^{7,3'CHO}$G[5']ppp[5']$m^7$G

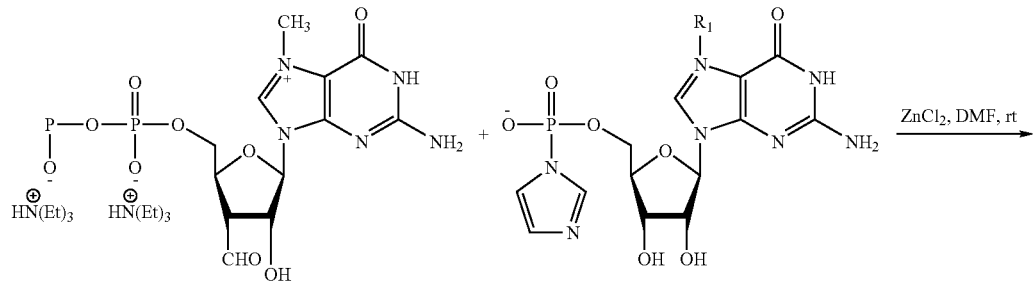

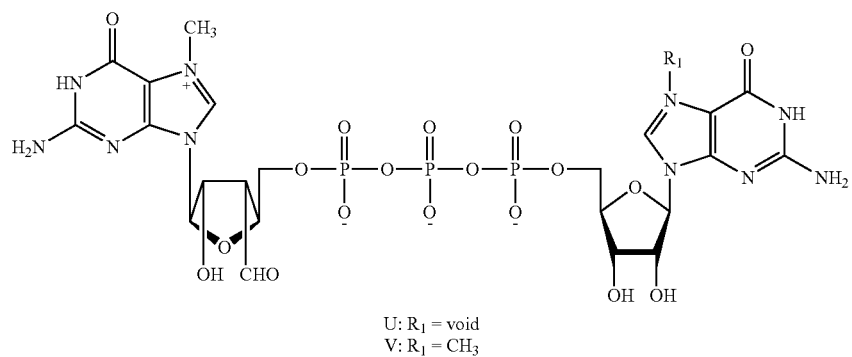

U: R₁ = void
V: R₁ = CH₃

The coupling reaction of $m^{7,3'CHO}$GDP (N7Me-3'CHOGDP) with Imidazolide GMP (ImGMP) or Imidazolide $m^7$GMP (m7-ImGMP) in the presence of $ZnCl_2$ as the catalyst affords the corresponding cap analogs U and V.

Example 29

Scheme to Make m$_2^{7,3'O}$G[5']ppp[5']$^{2'F}$G and m$_2^{7,3'O}$G[5']ppp[5']m$^{7,2'F}$G

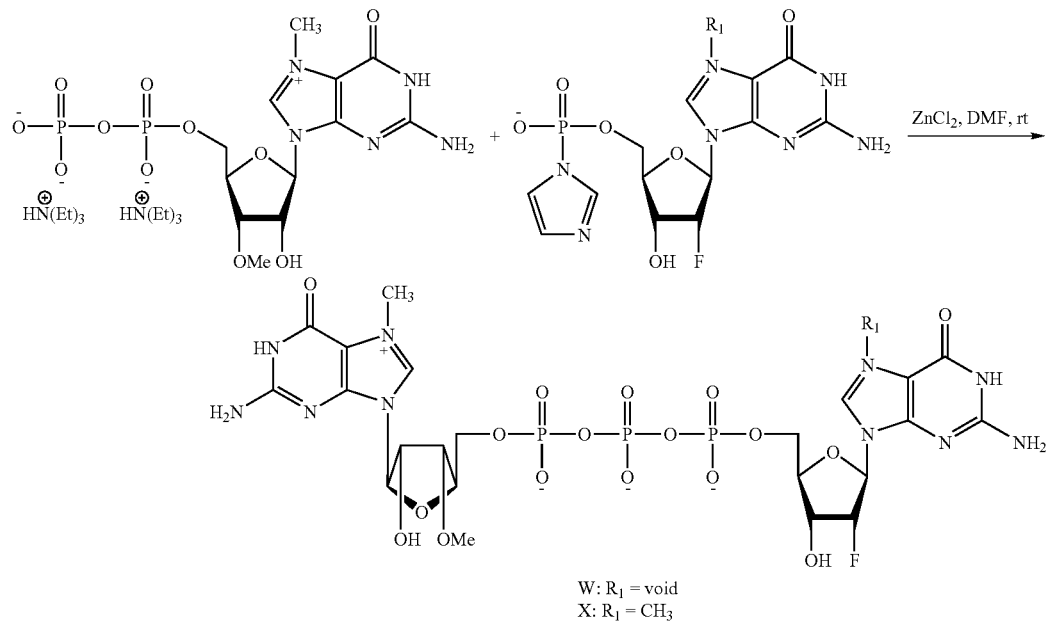

W: R$_1$ = void
X: R$_1$ = CH$_3$

The coupling reaction of m$_2^{7,3'O}$GDP (N7Me-3'OMeGDP) with Imidazolide $^{2'F}$GMP (Im2'FGMP) or Imidazolide m$^{7,2'F}$GMP (N7MeIm2'FGMP) in the presence of ZnCl$_2$ as the catalyst affords the corresponding cap analogs W and X.

Example 30

Scheme to Make m$^{7,3'F}$2'dG[5']ppp[5']G and m$^{7,3'S}$2'dG [5']G

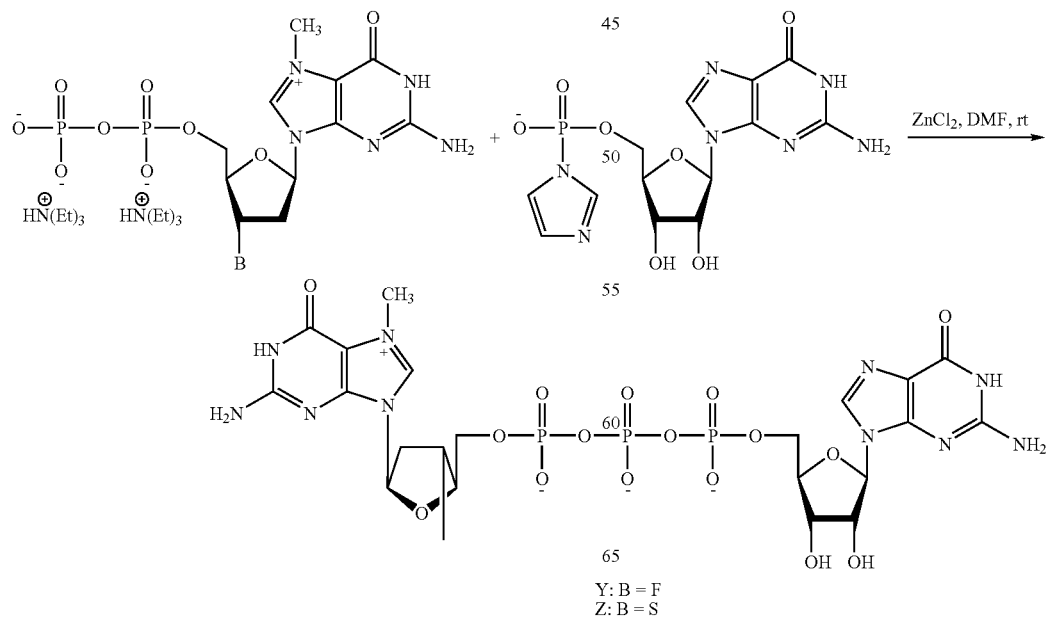

Y: B = F
Z: B = S

The coupling reaction of $m^{7,3'F}2'dGDP$ (N7Me-3'F-2'dGDP) or $m^{7,3'S}2'dGDP$ (N7Me-3'S-2'dGDP) with Imidazolide GMP (ImGMP) in the presence of $ZnCl_2$ as the catalyst affords the corresponding cap analogs Y and Z.

Example 31

Scheme to Make $m^{7,3'TBDMS}G[5']ppp[5']G$ and $m^{7,2'TBDMS}G[5']ppp[5']G$

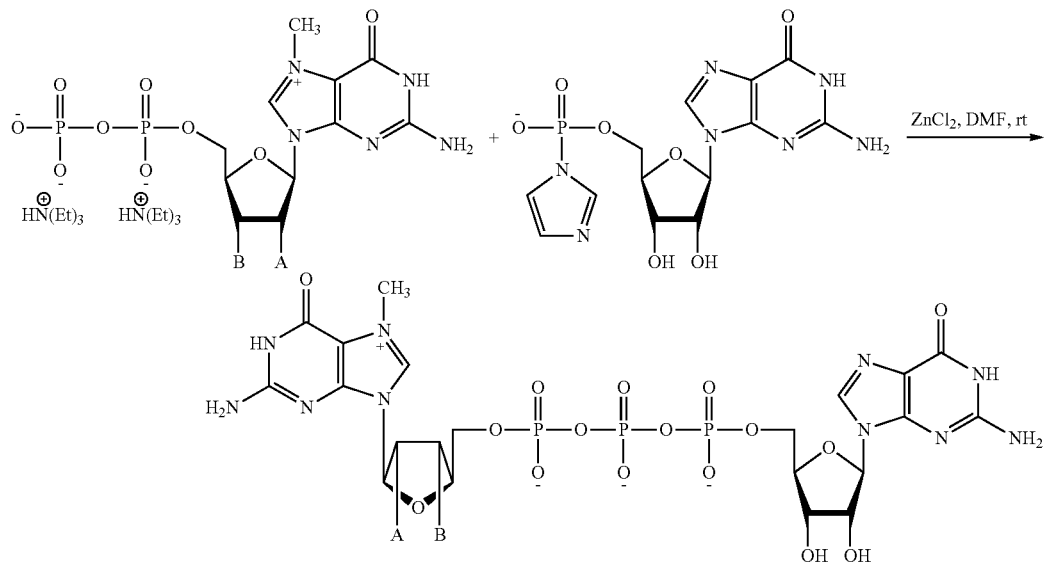

Aa: A = OH, B = TBDMS
Bb: A = TBDMS, B = OH

The coupling reaction of $m^{7,3'TBDMS}GDP$ (N7Me-3'BDMS-GDP) or $^{7,2'TBDMS}GMP$ (N7Me-2'BDMS-GMP) with Imidazolide GMP (ImGMP) in the presence of $ZnCl_2$ as the catalyst affords the corresponding cap analogs Aa and Bb.

Example 32

Scheme to Make $m^{7,LNA}G[5']ppp[5']G$ and $m^{7,LNA}G[5']ppp[5']m^7G$

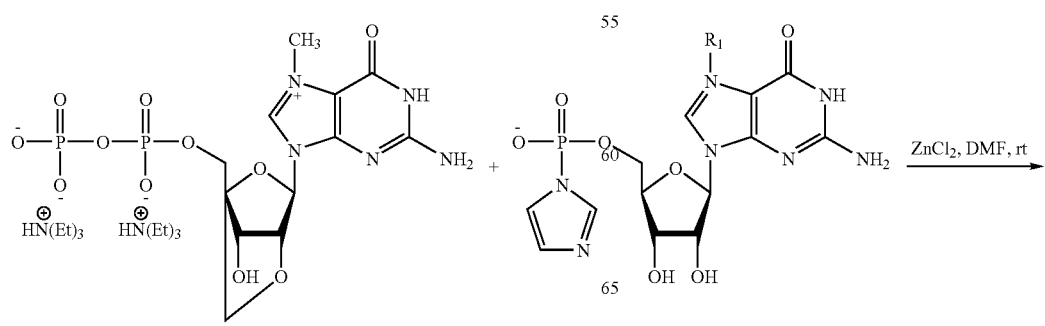

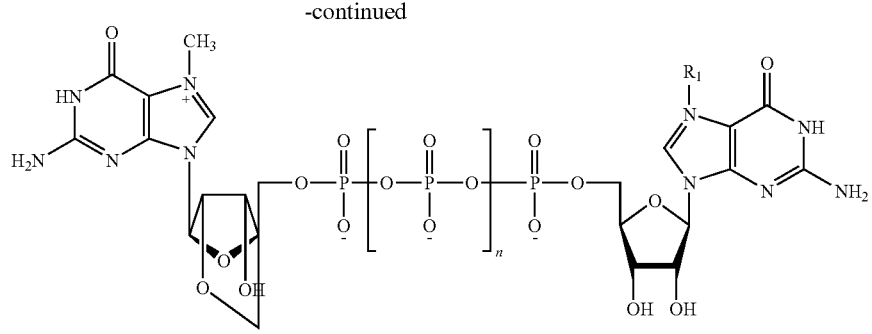

Cd: R₁ = void
Dd: R₁ = CH₃
n = 2
LNA = methylene bridge
between 2′O and 4′C

The coupling reaction of m$^{7,LNA}$GDP (N7Me-LNA-GDP) with Imidazolide GDP (ImGDP) or Imidazolide m$^7$GDP (m7-ImGDP) in the presence of ZnCl$_2$ as the catalyst affords the corresponding cap analogs Cc and Dd.

Example 33

Scheme to Make m$^{7,2'3'Isopropylidine}$G[5′]pppp[5′]G and m$^{7,2'3'Isopropylidine}$G[5′]pppp[5′]m$^7$G

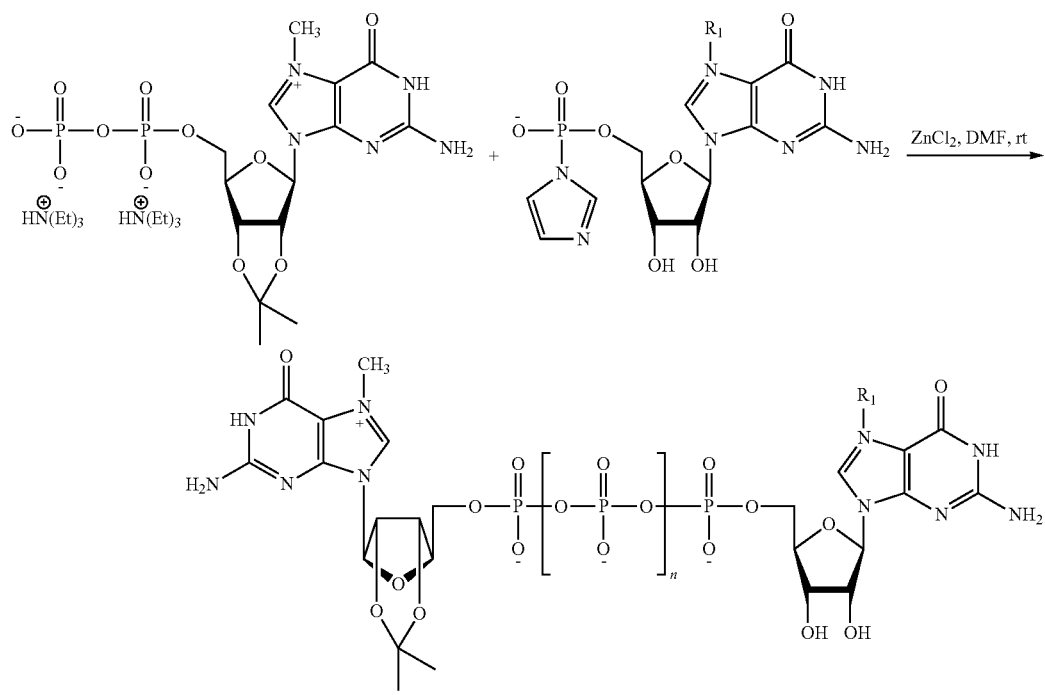

Ee: R₁ = void
Ff: R₁ = CH₃
n = 2

The coupling reaction of m$^{7,2'3'Isopropylidine}$GDP (N7Me-2′3′ isopropylideneGDP) with Imidazolide GDP (ImGDP) or Imidazolide m$^7$GDP (m7-ImGDP) in the presence of ZnCl$_2$ as the catalyst affords the corresponding cap analogs Ee and Ff.

Although the present disclosure is described with respect to certain embodiments and examples, various modifications may be made without departing from the spirit and scope of the invention.

---

---

What is claimed is:

1. A composition comprising

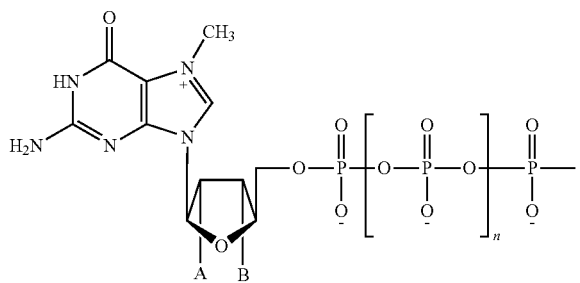

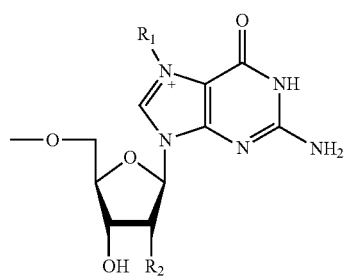

wherein
A is selected from a halogen, OH, $OCH_3$, H, tert-butyldimethylsilyl and 2',3'-O-isopropylidene;
B is selected from a halogen, OH, $OCH_3$, $NH_2$, $N_3$, $NO_2$, $CF_3$, CHO, S, tert-butyldimethylsilyl, LNA, and 2',3'-O-isopropylidene;
$R_1$ is $CH_3$ or void;
$R_2$ is selected from OH, $OCH_3$ and a halogen;
n is 1, 2 or 3;
when B is OH or $OCH_3$, $R_1$ is void and $R_2$ is OH, then A is neither OH nor $OCH_3$; and
wherein at least one of A or B is halogen.

2. The composition as recited in claim 1, wherein A, B, or $R_2$ is fluorine.

3. The composition as recited in claim 1 attached to the 5' end of an RNA molecule.

4. The composition as recited in claim 1 attached to the 5' end of an RNA molecule.

5. The composition as recited in claim 2 attached to the 5' end of an RNA molecule.

6. The composition as recited in claim 1, wherein:
A is selected from a halogen, OH, $OCH_3$, H, tert-butyldimethylsilyl and 2',3'-O-isopropylidene;
B is selected from a halogen, OH, $OCH_3$, $NH_2$, $N_3$, $NO_2$, CHO, S, tert-butyldimethylsilyl, LNA, and 2',3'-O-isopropylidene;
$R_1$ is void;
$R_2$ is selected from OH, $OCH_3$ and a halogen;
n is 1, 2 or 3;
when A is either OH or $OCH_3$, then $R_2$ is not OH; and
wherein A, B or $R_2$ is halogen.

7. The composition as recited in claim 6 attached to the 5' end of an RNA molecule.

8. The composition as recited in claim 1, wherein:
A is selected from a halogen, OH, $OCH_3$, H, -and 2',3'-O-isopropylidene;
B is selected from $CF_3$, OH, $OCH_3$, $NH_2$, $N_3$, $NO_2$, CHO, LNA, and 2',3'-O-isopropylidene;
$R_1$ is $CH_3$;
$R_2$ is selected from OH, $OCH_3$ and a halogen;
n is 1, 2 or 3,
when A is OH, $R_2$ is not OH; and
wherein A or $R_2$ is halogen.

9. The composition as recited in claim 8, wherein A or $R_2$ is fluorine.

10. The composition as recited in claim 8 attached to the 5' end of an RNA molecule.

11. The composition as recited in claim 9 attached to the 5' end of an RNA molecule.

12. A kit for capping an RNA transcript comprising:
a) an cap analog having the structure:

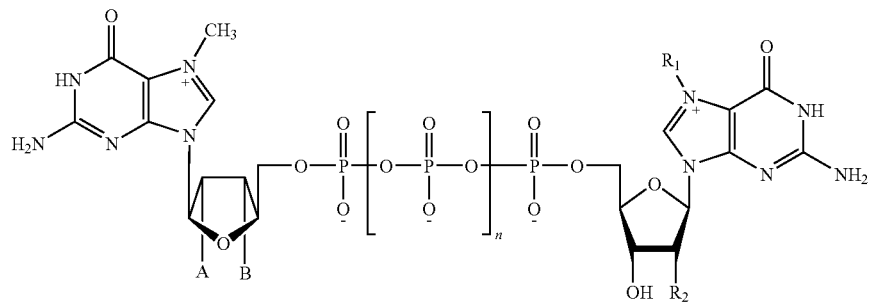

wherein:
A is selected from a halogen, OH, OCH$_3$, H, tert-butyldimethylsilyl and 2',3'-O-isopropylidene;
B is selected from a halogen, OH, OCH$_3$, NH$_2$, N$_3$, NO$_2$, CF$_3$, CHO, S, tert-butyldimethylsilyl, LNA, and 2',3'-O-isopropylidene;
R$_1$ is CH$_3$ or void;
R$_2$ is selected from OH, OCH$_3$ and a halogen;
n is 1, 2 or 3; and
when B is OH or OCH$_3$, R$_1$ is void and R$_2$ is OH, then A is neither OH nor OCH$_3$,
wherein at least one of A or B is halogen and
b) RNA polymerase.

13. A method of synthesizing a dinucleotide cap analog comprising:
a) providing a first guanosine comprising at least one of a 2' substituent and a 3' substituent on the ribose ring, wherein the 2' substituent is selected from a halogen, OCH$_3$, H, tert-butyldimethylsilyl and 2',3'-O-isopropylidene and the 3' substituent is OH and when the 3' substituent is selected from halogen, OH, OCH$_3$, NH$_2$, N$_3$, NO$_2$, CH$_3$, CHO, S, ter-buthyldimethylsilyl, LNA, and 2',3'-O-isopropylidene, the 2' substituent is OH, wherein at least one of the 2' substituent and the 3' substituent is a halogen
b) phosphorylating the first guanosine at least twice, forming a first nucleotide,
c) methylating the first guanosine at position N-7,
d) adding a second guanosine optionally comprising a 2' ribose ring substituent which is selected from OH, OCH$_3$, and a halogen, and
e) linking said first guanosine with said second guanosine, forming a dinucleotide cap analog.

14. The kit of claim 12 further comprising nucleotides, ribonuclease inhibitor, enzyme buffer or nucleotide buffer.

15. The method of claim 13 further comprising attaching said dinucleotide cap analog to the 5' end of an RNA molecule.

* * * * *

SEQUENCE LISTING

<160> NUMBER OF SEQ ID NOS: 1

<210> SEQ ID NO 1
<211> LENGTH: 10
<212> TYPE: RNA
<213> ORGANISM: Unknown
<220> FEATURE:
<223> OTHER INFORMATION: misc_signal

<400> SEQUENCE: 1
gccaccaugg                                                          10